US009861418B2

United States Patent
Matityahu et al.

(10) Patent No.: US 9,861,418 B2
(45) Date of Patent: Jan. 9, 2018

(54) IMPLANT INSERTION DEVICE WITH CONTINUOUSLY ADJUSTABLE TARGETING ASSEMBLY

(71) Applicant: EPIX ORTHOPAEDICS, INC., Los Altos, CA (US)

(72) Inventors: Amir M. Matityahu, Los Altos, CA (US); Benjamin Clawson, Santa Cruz, CA (US); Alan Grantz, Aptos, CA (US)

(73) Assignee: Epix Orthopaedics, Inc., Los Altos, CA (US)

( * ) Notice: Subject to any disclaimer, the term of this patent is extended or adjusted under 35 U.S.C. 154(b) by 140 days.

(21) Appl. No.: 13/763,599

(22) Filed: Feb. 8, 2013

(65) Prior Publication Data

US 2014/0052132 A1 Feb. 20, 2014

Related U.S. Application Data

(60) Provisional application No. 61/596,583, filed on Feb. 8, 2012.

(51) Int. Cl.
*A61F 5/00* (2006.01)
*A61B 17/88* (2006.01)
(Continued)

(52) U.S. Cl.
CPC ...... *A61B 17/8872* (2013.01); *A61B 17/1725* (2013.01); *A61B 17/72* (2013.01);
(Continued)

(58) Field of Classification Search
CPC ..... A61B 17/17; A61B 17/72; A61B 17/1739; A61B 17/1764; A61B 17/155; A61B 17/1717
(Continued)

(56) References Cited

U.S. PATENT DOCUMENTS 2,181,746 A * 11/1939 Siebrandt ................ 606/96
2,441,765 A    5/1948 Hopkins
(Continued)

FOREIGN PATENT DOCUMENTS

CN    101686836 A    3/2010
CN    101754723 A    6/2010
(Continued)

OTHER PUBLICATIONS

International Search Report issued by Intellectual Property Organization for PCT/US2013/025455, dated Jul. 1, 2013, pp. 1-6.
(Continued)

*Primary Examiner* — Eduardo C Robert
*Assistant Examiner* — Tara R Carter
(74) *Attorney, Agent, or Firm* — Intellectual Innovations Legal Advisors

(57) ABSTRACT

An implant insertion device including a body having a first portion for coupling to a proximal end of an intramedullary rod and a second portion extending in a spaced position from the intramedullary rod in the vicinity of an aperture in a proximal end of the rod when the rod is coupled to the first portion. The second portion can include a targeting assembly having a passageway for receiving a guide sleeve and for pivoting the guide sleeve relative to the aperture through an angular range for inserting the fastener into the aperture of the rod. An implant insertion device for use with an implantable device is additionally provided.

21 Claims, 12 Drawing Sheets

(51) Int. Cl.
*A61B 17/17* (2006.01)
*A61B 17/72* (2006.01)
*A61B 17/74* (2006.01)

(52) U.S. Cl.
CPC ........ *A61B 17/7241* (2013.01); *A61B 17/744* (2013.01); *A61B 17/748* (2013.01)

(58) Field of Classification Search
USPC .................... 606/86 R, 96–98, 62–68, 87
See application file for complete search history.

(56) References Cited

U.S. PATENT DOCUMENTS

| | | | |
|---|---|---|---|
| 3,308,812 A | 3/1967 | Gidlund | |
| 3,783,860 A | 1/1974 | Burstein et al. | |
| 4,519,100 A | 5/1985 | Wills et al. | |
| 4,622,959 A * | 11/1986 | Marcus | 606/64 |
| 4,653,487 A | 3/1987 | Maale | |
| 4,657,001 A | 4/1987 | Fixel | |
| 4,733,654 A | 3/1988 | Marino | |
| 4,776,330 A | 10/1988 | Chapman et al. | |
| 4,827,917 A | 5/1989 | Brumfield | |
| 4,846,162 A | 7/1989 | Moehring | |
| 4,875,475 A * | 10/1989 | Comte et al. | 606/64 |
| 4,881,535 A | 11/1989 | Sohngen | |
| 5,032,125 A | 7/1991 | Durham et al. | |
| 5,041,114 A | 8/1991 | Chapman et al. | |
| 5,047,034 A | 9/1991 | Sohngen | |
| 5,127,913 A | 7/1992 | Thomas, Jr. | |
| 5,167,663 A | 12/1992 | Brumfield | |
| 5,176,681 A | 1/1993 | Lawes et al. | |
| 5,190,544 A | 3/1993 | Chapman et al. | |
| 5,248,313 A | 9/1993 | Greene et al. | |
| 5,295,991 A * | 3/1994 | Frigg | 606/62 |
| 5,429,640 A | 7/1995 | Shuler et al. | |
| 5,454,813 A | 10/1995 | Lawes | |
| 5,514,137 A | 5/1996 | Coutts | |
| 5,562,667 A | 10/1996 | Shuler et al. | |
| 5,772,662 A | 6/1998 | Chapman et al. | |
| 5,935,127 A | 8/1999 | Border | |
| 6,120,504 A | 9/2000 | Brumback et al. | |
| 6,123,708 A | 9/2000 | Kilpela et al. | |
| 6,126,661 A | 10/2000 | Faccioli et al. | |
| 6,221,074 B1 | 4/2001 | Cole et al. | |
| 6,235,031 B1 | 5/2001 | Hodgeman et al. | |
| 6,402,753 B1 | 6/2002 | Cole et al. | |
| 6,406,477 B1 | 6/2002 | Fujiwara | |
| 6,443,954 B1 | 9/2002 | Bramlet et al. | |
| 6,488,684 B2 | 12/2002 | Bramlet et al. | |
| 6,562,042 B2 | 5/2003 | Nelson | |
| 6,648,889 B2 | 11/2003 | Bramlet et al. | |
| 6,702,816 B2 | 3/2004 | Buhler et al. | |
| 6,783,529 B2 | 8/2004 | Hover et al. | |
| 6,860,691 B2 | 3/2005 | Unsworth et al. | |
| 6,893,443 B2 | 5/2005 | Frigg et al. | |
| 6,926,719 B2 | 8/2005 | Sohngen et al. | |
| 7,001,386 B2 | 2/2006 | Sohngen et al. | |
| 7,008,425 B2 | 3/2006 | Phillips | |
| 7,041,104 B1 | 5/2006 | Cole et al. | |
| 7,267,678 B2 | 9/2007 | Medoff | |
| 7,601,153 B2 | 10/2009 | Shinjo et al. | |
| 7,670,340 B2 | 3/2010 | Brivio et al. | |
| 7,771,428 B2 | 8/2010 | Siravo et al. | |
| 7,972,336 B2 | 7/2011 | James et al. | |
| 8,100,911 B2 | 1/2012 | Yamazaki et al. | |
| 8,790,343 B2 | 7/2014 | Mcclellan et al. | |
| 2002/0133156 A1 | 9/2002 | Cole | |
| 2002/0151898 A1 | 10/2002 | Sohngen et al. | |
| 2002/0156473 A1 | 10/2002 | Bramlet et al. | |
| 2003/0036758 A1 | 2/2003 | Frigg et al. | |
| 2003/0114855 A1 | 6/2003 | Wahl et al. | |
| 2004/0106922 A1 | 6/2004 | Snyder | |
| 2005/0010226 A1 | 1/2005 | Grady et al. | |
| 2005/0055023 A1 | 3/2005 | Sohngen et al. | |
| 2005/0085812 A1 | 4/2005 | Sherman et al. | |
| 2005/0149025 A1 | 7/2005 | Ferrante et al. | |
| 2005/0182405 A1 | 8/2005 | Orbay et al. | |
| 2005/0182406 A1 | 8/2005 | Orbay et al. | |
| 2005/0234457 A1 | 10/2005 | James et al. | |
| 2006/0015101 A1 | 1/2006 | Warburton et al. | |
| 2006/0058887 A1 | 3/2006 | DeSmet et al. | |
| 2006/0069392 A1 | 3/2006 | Renzi et al. | |
| 2006/0106398 A1 | 5/2006 | Lauryssen et al. | |
| 2006/0122600 A1 | 6/2006 | Cole et al. | |
| 2007/0049938 A1 | 3/2007 | Wallace et al. | |
| 2007/0049939 A1 | 3/2007 | Wallace et al. | |
| 2007/0049940 A1 | 3/2007 | Wallace et al. | |
| 2007/0100343 A1 | 5/2007 | Cole et al. | |
| 2007/0123876 A1 | 5/2007 | Czartoski et al. | |
| 2007/0123878 A1 | 5/2007 | Shaver et al. | |
| 2007/0162016 A1 | 7/2007 | Matityahu | |
| 2007/0179835 A1 | 8/2007 | Ott et al. | |
| 2007/0233100 A1 | 10/2007 | Metzinger | |
| 2007/0233101 A1 | 10/2007 | Metzinger | |
| 2007/0233102 A1 | 10/2007 | Metzinger | |
| 2007/0233103 A1 | 10/2007 | Metzinger | |
| 2007/0233104 A1 | 10/2007 | Metzinger | |
| 2007/0270845 A1 | 11/2007 | Watanabe et al. | |
| 2007/0270846 A1 | 11/2007 | Metzinger | |
| 2007/0276385 A1 | 11/2007 | Schlienger et al. | |
| 2008/0039845 A1 | 2/2008 | Bonutti et al. | |
| 2008/0091203 A1 | 4/2008 | Warburton et al. | |
| 2008/0140077 A1 | 6/2008 | Kebaish | |
| 2008/0147066 A1 | 6/2008 | Longsworth et al. | |
| 2008/0147067 A1 | 6/2008 | Phillips | |
| 2008/0161805 A1 | 7/2008 | Saravia et al. | |
| 2008/0287949 A1 | 11/2008 | Keith et al. | |
| 2009/0048598 A1 | 2/2009 | Ritchey et al. | |
| 2009/0048600 A1 | 2/2009 | Matityahu et al. | |
| 2009/0069816 A1* | 3/2009 | Sasing | A61B 17/1725 606/96 |
| 2009/0306666 A1 | 12/2009 | Czartoski et al. | |
| 2010/0094293 A1 | 4/2010 | Mcclellan et al. | |
| 2010/0160913 A1* | 6/2010 | Scaglia | A61B 17/1725 606/57 |
| 2010/0179550 A1 | 7/2010 | Schreiber et al. | |
| 2010/0211112 A1 | 8/2010 | Kuster et al. | |
| 2010/0268229 A1 | 10/2010 | Siravo et al. | |
| 2011/0066152 A1 | 3/2011 | Keller et al. | |
| 2011/0295255 A1 | 12/2011 | Roberts et al. | |
| 2012/0109128 A1 | 5/2012 | Frigg | |

FOREIGN PATENT DOCUMENTS

| | | |
|---|---|---|
| EP | 0696441 A2 | 2/1996 |
| EP | 0845245 A2 | 6/1998 |
| EP | 1356777 A2 | 10/2003 |
| EP | 1557131 A1 | 7/2005 |
| EP | 1639953 A1 | 3/2006 |
| GB | 2387112 A | 10/2003 |
| JP | 2005270503 A | 10/2005 |
| JP | 2007143942 A | 6/2007 |
| JP | 2010530791 A | 9/2010 |
| WO | 97/39693 | 10/1997 |
| WO | WO-03053265 A1 | 7/2003 |
| WO | WO-2004096067 A2 | 11/2004 |
| WO | WO-2005092219 A1 | 10/2005 |
| WO | WO-2005094707 A2 | 10/2005 |
| WO | WO-2006066440 A2 | 6/2006 |
| WO | 2006/916525 | 8/2006 |
| WO | WO-2008089096 A2 | 7/2008 |
| WO | 2008/146150 | 12/2008 |
| WO | 2009/002890 | 12/2008 |

OTHER PUBLICATIONS

Written Opinion issued by World Intellectual Property Organization for PCT/US2013/025455, dated Jul. 1, 2013, pp. 1-9.
EPO Communication dated Sep. 16, 2014 for European Application No. 13706828.4 requiring a response to the Written Opinion issued for the parent PCT application.
International Preliminary Report on Patentability for Application No. PCT/US2013/025455, dated Aug. 12, 2014, pp. 1-10.

(56) References Cited

OTHER PUBLICATIONS

Response mailed Mar. 26, 2015 for EPO communication dated Sep. 16, 2014 for European Application No. 13706828.4 filed Feb. 8, 2013.
Advisory Action and Response After Final dated Nov. 9, 2011 for U.S. Appl. No. 12/143,798, filed Jun. 22, 2008, pp. 1-4.
Advisory Action and Response after Final dated Nov. 14, 2012 for U.S. Appl. No. 12/576,210, filed Oct. 8, 2009, pp. 1-3.
Applicant Initiated Interview Summary dated Dec. 2, 2011 for U.S. Appl. No. 12/143,798, filed Jun. 22, 2008, pp. 1-3.
Applicant Initiated Interview Summary dated Jun. 24, 2014 for U.S. Appl. No. 12/143,798, filed Jun. 22, 2008, pp. 1-4.
Applicant-Initiated Interview Summary dated Feb. 25, 2014 for U.S. Appl. No. 12/576,210, filed Oct. 8, 2009, pp. 1-3.
DePuy Orthopaedics, Inc., Surgical Technique, Femoral Troch Entry Nailing System Options Made Easy, Versanail Femoral Troch Entry, Brochure, DePuy, a Johnson-Johnson Company, 2006, pp. 1-20.
English Translation of Notice to File Response dated Jul. 3, 2014 for Korean Patent Application No. 1020107001583 filed Jun. 22, 2008, pp. 1-8.
Examination Report dated Apr. 9, 2015 for European Patent Application No. 08780913.3 filed Dec. 22, 2006, pp. 1-4.
Examination Report dated Nov. 20, 2014 for European Patent Application No. 08780913.3 filed Dec. 22, 2006, pp. 1-4.
Examination Report dated Jul. 24, 2014 for Canadian Patent Application No. 2690786 filed Jun. 22, 2008, pp. 1-2.
Examiner Initiated Interview Summary dated Jun. 2, 2011 for U.S. Appl. No. 12/143,798, filed Jun. 22, 2008, pp. 1-4.
Extended European Search Report dated Jun. 21, 2013 for European Patent Application No. 08780913.3 filed Dec. 22, 2006, pp. 1-5.
Final Office Action dated Feb. 1, 2017 for U.S. Appl. No. 14/555,232, filed Sep. 26, 2014, pp. 1-9.
Final Office Action dated Jul. 29, 2012 for U.S. Appl. No. 12/576,210, filed Oct. 8, 2009, pp, 1-13.
Final Office Action dated Aug. 31, 2011 for U.S. Appl. No. 12/143,798, filed Jun. 22, 2008, pp. 1-29.
First Instructional Letter dated Jun. 6, 2011 in Response to Office Action dated Mar. 3, 2011 for Chinese Patent Application No. 200880025286.1, pp. 1-5.
First Patent Examination Report issued by the Australian Patent Office for Australian Patent Application Serial No. 2008268507, dated Dec. 4, 2012, pp. 1-4.
International Preliminary Report on Patentability for Application No. PCT/US2008/067818, dated Dec. 22, 2009, pp. 1-5.
International Preliminary Report on Patentability for Application No. PCT/US2009/060067, dated Apr. 12, 2011, pp. 1-6.
International Search Report for Application No. PCT/US2008/067818 dated Oct. 8, 2008, pp. 1.
International Search Report for Application No. PCT/US2009/060067, dated Dec. 17, 2009, pp, 1-2.
Non-Final Office Action dated Dec. 8, 2011 for U.S. Appl. No. 12/576,210, filed Oct. 8, 2009, pp. 1-18.
Non-Final Office Action dated Jun. 16, 2016 for U.S. Appl. No. 14/555,232, filed Sep. 26, 2014, pp. 1-9.
Non-Final Office Action dated Feb. 22, 2011 for U.S. Appl. 12/143,798, filed Jun. 22, 2008, pp. 1-17.
Non-Final Office Action dated Apr. 23, 2014 for U.S. Appl. No. 12/143,798, filed Jun. 22, 2008, pp. 1-16.
Non-Final Office Action dated Oct. 23, 2013 for U.S. Appl. No. 12/576,210, filed Oct. 8, 2009, pp. 1-17.
Notice of Allowance and Examiner-Initiated Interview Summary dated Mar. 26, 2014 for U.S. Appl. No. 12/576,210, filed Oct. 8, 2009, pp. 1-12.
Notice of Allowance dated Jul. 31, 2014 for U.S. Appl. No. 12/143,798, filed Jun. 22, 2008, pp. 1-7.
Office Action dated Jan. 12, 2017 for Japanese Patent Application No. 2014-556760, pp. 1-7 (with Translation).
Office Action dated May 24, 2016 for Chinese Patent Application No. 201380016394.3, pp. 1-25 (with Translation).

Requirement for Restriction/Election dated Mar. 11, 2016 for U.S. Appl. No. 14/555,232, filed Sep. 26, 2014, pp. 1-9.
Requirement for Restriction/Election dated Mar. 19, 2014 for U.S. Appl. No. 12/143,798, filed Jun. 22, 2008, pp. 1-9.
Response dated Jan. 3, 2014 for Extended European Search Report dated Jun. 21, 2013 for European Patent Application No. 08780913.3 filed Dec. 22, 2006, pp. 1-8.
Response dated Jun. 3, 2011 for Non-Final Office Action dated Feb. 22, 2011 for U.S. Appl. No. 12/143,798, filed Jun. 22, 2008, pp. 1-16.
Response dated Apr. 8, 2014 for Requirement for Restriction/Election dated Mar. 19, 2014 for U.S. Appl. No. 12/143,798, filed Jun. 22, 2008, pp. 1-7.
Response dated Jun. 8, 2012 for Non-Final Office Action dated Dec. 8, 2011 for U.S. Appl. No. 12/576,210, filed Oct. 8, 2009, pp. 1-14.
Response dated Oct. 14, 2011 for Final Office Action dated Aug. 31, 2011 for U.S. Appl. No. 12/143,798, filed Jun. 22, 2008, pp. 1-17.
Response dated Dec. 15, 2016 for Non-Final Office Action dated Jun. 16, 2016 for U.S. Appl. No. 14/555,232, filed Sep. 26, 2014, pp. 1-14.
Response dated Apr. 20, 2015 for Examination Report dated Jul. 24, 2014 for Canadian Patent Application No. 2690786 filed Jun. 22, 2008, pp. 1-16.
Response dated Feb. 21, 2014 for Non-Final Office Action dated Oct. 23, 2013 for U.S. Appl. No. 12/576,210, filed Oct. 8, 2009, pp. 1-10.
Response dated Jun. 22, 2014 for Non-Final Office Action dated Apr. 23, 2014 for U.S. Appl. No. 12/143,798, filed Jun. 22, 2008, pp. 1-17.
Response dated Mar. 23, 2016 for Restriction Requirement/Election dated Mar. 11, 2016 for U.S. Appl. No. 14/555,232, filed Sep. 26, 2014, pp. 1-5.
Response dated Oct. 24, 2012 for Final Office Action dated Jul. 19, 2012 for U.S. Appl. No. 12/576,210, filed Oct. 8, 2009, pp. 1-10.
Response dated Apr. 30, 2014 for Examination Report dated Dec. 4, 2012 for Australian Patent Application No. 2008268507 filed Jun. 22, 2006, pp. 1-27.
Response dated Mar. 30, 2015 for Examination Report dated Nov. 20, 2014 for European Patent Application No. 08780913.3 filed Dec. 22, 2006, pp. 1-10.
Response dated Oct. 30, 2014 for Notice of Allowance dated Jul. 31, 2014 for U.S. Appl. No. 12/143,798, filed Jun. 22, 2008, pp. 1-3.
Response dated on Jan. 3, 2014 for European office actions dated Jul. 9, 2013 and Jun. 21, 2013 for Application No. EP08780913.3 filed Jun. 22, 2008, pp. 1-9.
Second Instructional Letter dated Jul. 5, 2011 in Response to Office Action dated Mar. 3, 2011 for Chinese Patent Application No. 200880025286.1, pp. 1-5.
Second Response dated Nov. 30, 2011 for Final Office Action dated Aug. 31, 2011 and the Advisory Action dated Nov. 9, 2011 for U.S. Appl. No. 12/143,798, filed Jun. 22, 2008, pp. 1-18.
Stryker Product, Gamma3—The Compact Version of the Gamma Nail System—Operative Technique: Hip Fracture System Trochanteric and Long Nails, Brochure, Literature No. LG3-0T Rev, 1, 10M 10/04, Stryker, 2004, pp. 1-44, Retrieved from the internet<www.stryker.com>.
Translation of Dec. 6, 2012 Office Action issued by Japanese Patent Office for corresponding Japanese patent application No. 2010513479 filed Jun. 22, 2008, pp. 1-3.
Translation of Sep. 14, 2013 Office Action issued by Japanese Patent Office for corresponding Japanese patent application No. 2010513479 filed Jun. 22, 2008, pp. 1.
Translation of Feb. 20, 2014 Office Action issued by Japanese Patent Office for corresponding Japanese patent application No. 2010513479 filed Jun. 22, 2008, pp. 1.
Translation of Office Action dated Mar. 3, 2011 for Chinese Patent Application No. 200880025286.1, pp. 1-10.
Written Opinion for Application No. PCT/US2008/067818, dated Oct. 8, 2008, pp. 1-4.
Written Opinion for Application No. PCT/US2009/060067, dated Dec. 17, 2009, pp. 1-5.

* cited by examiner

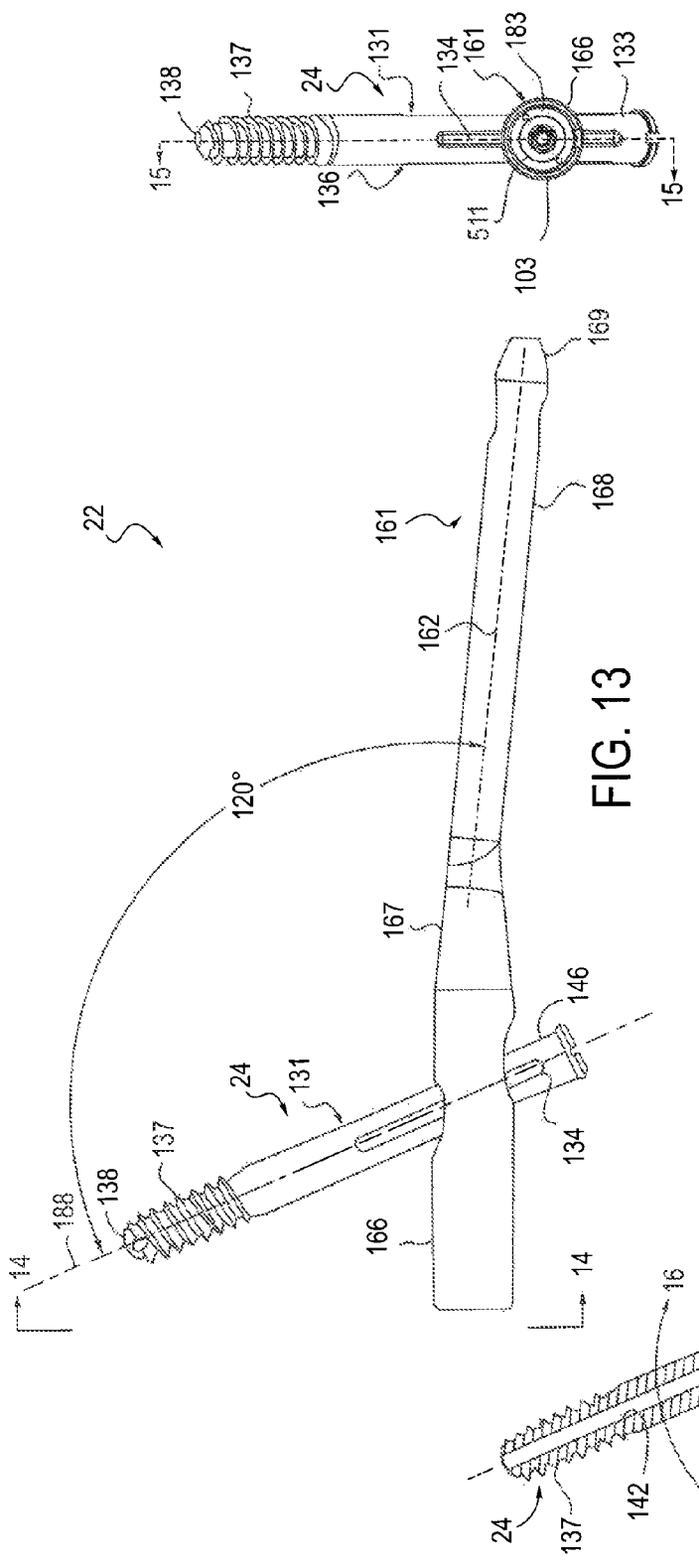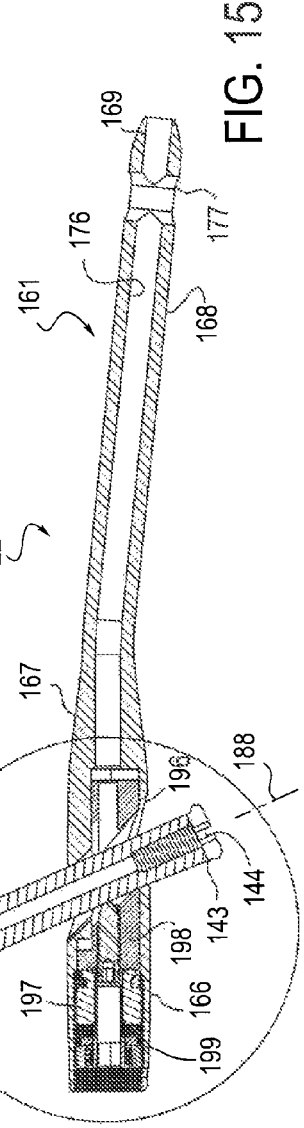
FIG. 13
FIG. 14
FIG. 15

US 9,861,418 B2

IMPLANT INSERTION DEVICE WITH CONTINUOUSLY ADJUSTABLE TARGETING ASSEMBLY

CROSS REFERENCE TO RELATED APPLICATION

The application claims priority to U.S. provisional application Ser. No. 61/596,583 filed Feb. 8, 2012, the entire content of which is incorporated herein by this reference.

FIELD OF THE INVENTION

The present invention relates to implant insertion devices for use with apparatus for affixing to bones and, more particularly, to a targeting guide for use with an intramedullary nail.

BACKGROUND OF THE INVENTION

Intramedullary rods or nails have been used to treat femoral, tibial, humeral and other bone fractures. Moreover, they have been used for fusions and repairs of unhealed or crooked bones. Femur, tibia, and humerus fractures, for example, have been treated with rod assemblies that for example are inserted into the canal to coapt the fractured parts. Peritrochanteric fractures of the femur, for example, have been treated with femoral rod assemblies that for example are inserted into the femoral canal to coapt the femur fractured parts. One or two angled cross-nails or locking screws are inserted through the bone at the proximal and distal ends of the intramedullary rod. Rods have been provided that permit the angle of the proximal screw relative to the rod to be adjusted in situ.

Implant insertion devices, such as targeting guides, have been provided for introducing intramedullary rods into bones, such as the femur, tibia, humerus, and between bones such as the calcaneus-talus-tibia or femur-tibia. Such devices can align a guide sleeve, with a locking screw inserted through the guide sleeve, relative to the bone so as to insert the screw into the nail and bone. Several implant insertion devices may be needed to accommodate for different angles between the screw, which is inserted through the nail, and the nail itself, because such devices typically provide only a single angle between the screw and the nail. Some implant insertion devices require disassembly of at least a portion of the device to remove a first insert with a first static angle for the guide sleeve and provide a second insert with a second static angle for the guide sleeve in order to change the angle at which the guide sleeve and locking screw are aligned relative to the nail. Some implant insertion devices require the guide sleeve to be removed, be uncoupled and rotated transversely into a constrained location in a stepwise manner in order to allow for, at most, a fixed five degree incremental step wise change from 120 degrees to 125 degrees to 130 degrees to 135 degrees without the ability to dynamically move throughout the range of angles in a smooth, continuous or non-incremental manner.

There is a need for an improved implant insertion device which permits the angle of the guide sleeve, and locking screw secured to the distal end of the guide sleeve, to be continuously adjusted on the device over a range of angles without removing the guide sleeve from the device or disassembling any portion of the device.

BRIEF DESCRIPTION OF THE DRAWINGS

The drawings described herein are for illustration purposes only and are not intended to limit the scope of the present disclosure in any way.

FIG. 13 is a rear view of an embodiment of the intramedullary rod with a pivotable fastener for use with the implant insertion device of FIG. 1.

FIG. 14 is a top end view of the intramedullary rod with a pivotable fastener of FIG. 13 taken along the line 14-14 of FIG. 13.

FIG. 15 is a cross-sectional view of the intramedullary rod with a pivotable fastener of FIG. 13 taken along the line 15-15 of FIG. 14.

DETAILED DESCRIPTION OF THE INVENTION

In general, an apparatus or device is provided for inserting an implant such as an intramedullary nail and related fasteners into a bone of a mammalian body for treating fractures, nonunions or malunions of the bone. It may also be used for fusion across bones such as the femur-tibia and calcaneus-talus-tibia. The device includes a targeting assembly for continuous or dynamic adjustment of the angle of a guide or alignment sleeve, and the fastener carried thereby, relative to an aperture in the implant for receiving the fastener. The apparatus or device of the present invention can also be referred to as an implant insertion device, a dynamic targeting mechanism, a targeting guide, a nail targeting device, a jig and other similar or suitable names.

Figure 1:
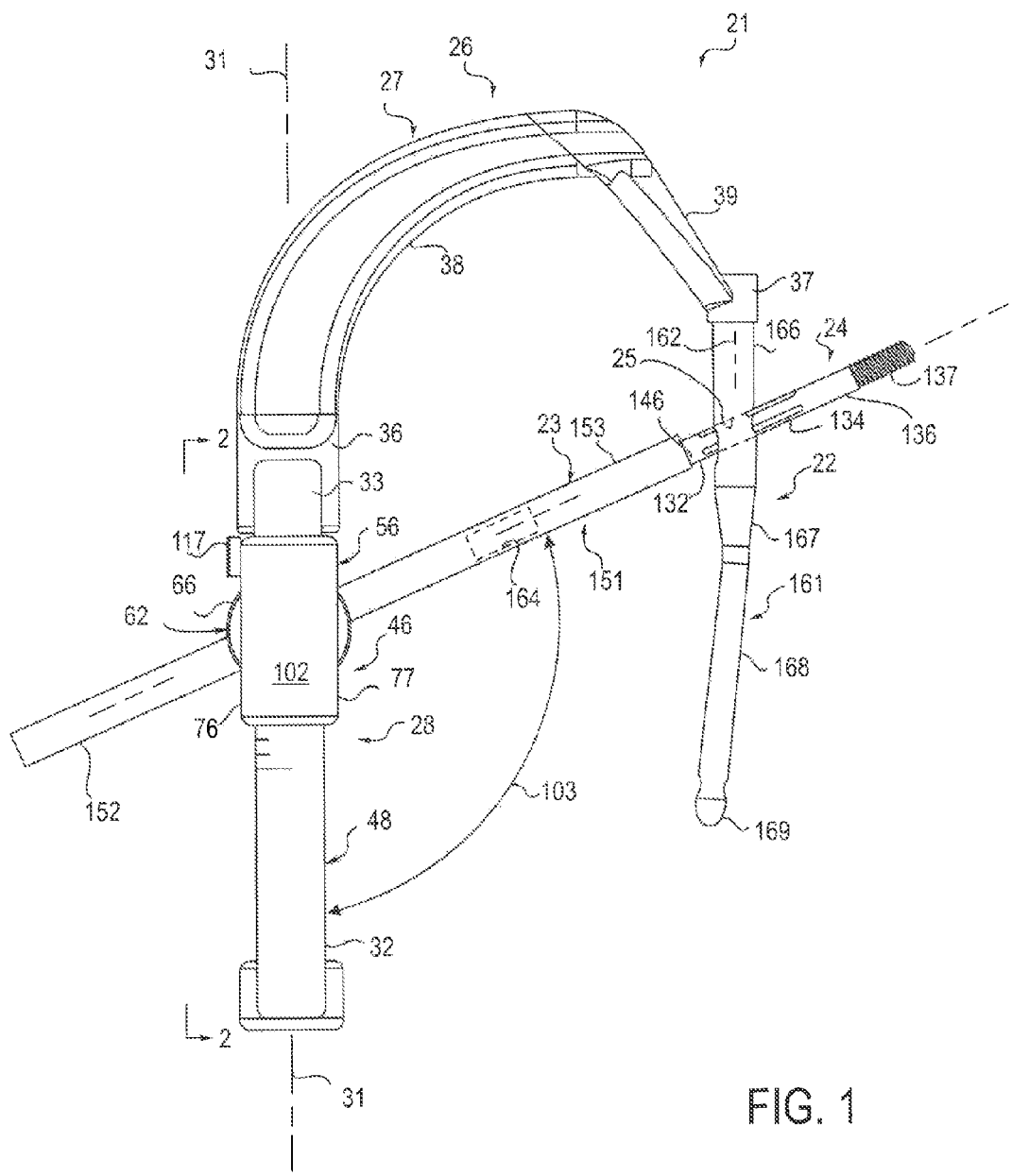
FIG. 1 is a side plan view of an implant insertion device of the present invention with the continuously adjustable targeting assembly in a first position and coupled to an intramedullary rod with a pivotable fastener.

In one embodiment of the invention, apparatus or implant insertion device 21 illustrated in FIG. 1, which can be made of any suitable material such as stainless steel, titanium, alloys, plastics, carbon fibers, or any composite or mesh materials, is provided for use with a suitable implant or implantable device such as an intramedullary rod or nail 22, a suitable alignment or guide sleeve 23 and a suitable fastener such as a fixation, lag or locking screw 24. Device 21 and guide sleeve 23 can be used to place screw 24 into the rod 22 once the rod 22 has been implanted into a bone of a mammalian body or before its implantation. Intramedullary rod 22 includes an aperture 25 for receiving screw 24 and the rod 22 is configured to permit the screw 24 to pivot in aperture 25 relative to the rod 22. Device 21 includes a body 26 having a first or arm portion 27 and a second or targeting portion 28. In one embodiment, targeting portion 28 is elongate and linear, extends along a longitudinal axis 31 and has a first or bottom portion 32 and a second or a top portion 33. The bottom portion 32 can be referred to as first end portion 32 and the top portion 33 can be referred to as a second end portion 33. Arm portion or arm 27 in one embodiment is arcuate so as to resemble an arch and has a first end portion or first extremity 36 coupled or joined to top portion 33 of targeting portion 28 by any suitable mean and a second end portion, second extremity or connector 37 adapted for coupling to the top or proximal end portion of intramedullary rod 22. The arm 27 can be made from any suitable material such as stainless steel, carbon fiber, plastic or composite materials, and in one embodiment includes an arcuate member or top arch 38 which extends from first end portion 36 of the arm 27 and an elongate member or gooseneck 39 which extends from the upper end of top arch 38 to the connector 37. When insertion device 21 is coupled to rod 22, as illustrated in FIG. 1, targeting portion 28 is spaced from and generally extends parallel to rod 22. In one embodiment, the targeting portion 28 is spaced from rod 22 at least in the vicinity of aperture 25 of the rod 22.

The targeting portion 28 includes a targeting assembly or mechanism 46 for receiving guide sleeve 23 and in one embodiment for pivoting the guide sleeve relative to the targeting portion, rod 22 and aperture 25 in intramedullary rod 22 through an angular range. The mechanism 46 serves to point guide sleeve 23, fastener 24 and in one embodiment both the guide sleeve 23 and the fastener 24 towards the intramedullary rod and more specifically towards the aperture 25 in the rod. In one embodiment, the mechanism and hence the device 21 serves to point the guide sleeve 23, the fastener 24 or the combination of the guide sleeve and the fastener towards the rod and in one embodiment the aperture 25 in the rod throughout or continuously over such angular range. Any suitable apparatus, mechanism or assembly can be provided for so pivoting the guide sleeve, the fastener or the combination of the guide sleeve and fastener. In one embodiment, targeting assembly includes a first elongate element or rail 47 and a second elongate element or rail 48 extending along longitudinal axis 31 in spaced-apart positions (see FIG. 2). First and second rails 47, 48 extend parallel to each other and are spaced apart from each other. Each of the longitudinally-extending rails 47, 48 can resemble a planar strip or bar. Each can be made from any suitable material such as stainless steel, metal, composite materials, plastic, carbon fiber or other fibers. First rail 47 has an inner planar surface 51, illustrated in FIG. 3, and second rail 48 has an inner planar surface 52, illustrated in FIG. 4, which face each other and extend parallel to each other.

Figure 7:
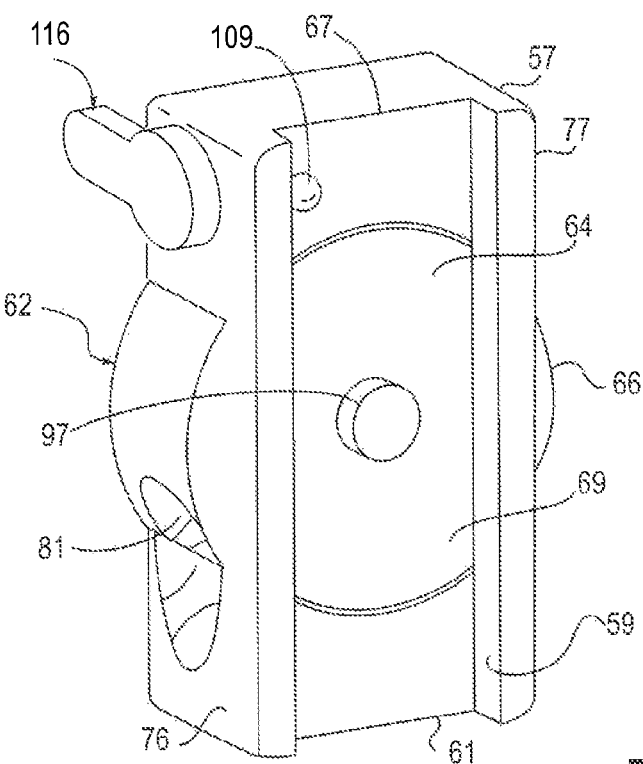
FIG. 7 is a first side perspective view of a portion of the continuously adjustable targeting assembly of the implant insertion device of FIG. 1 with a portion of the housing removed.

Targeting assembly 46 includes a carriage assembly or carriage 56 that can be slidably carried by first and second rails 47, 48. The carriage 56 includes a slide 57 made from any suitable material such as stainless steel and that is sized and shaped to more upwardly and downwardly along longitudinal axis 31 between rails 47 and 48. In one embodiment, shown for example in FIGS. 7 and 8, the slide 57 includes a planar first side surface 58 for slidably engaging inner elongate surface 51 of the first rail 47. Slide 57 further includes a cutout 59 for slidably receiving second rail 48 and assisting in the centering of slide 57 during its longitudinal travel along the rails 47 and 48. The planar second side surface 61 of the slide, which forms the base of cutout 59, extends parallel to first side surface 58 and slidably engages inner elongate surface 52 of the second rail 48.

A targeting element 62 can be rotatably carried by slide 57. In one embodiment, the targeting element 62 can be a disk, wheel or any other suitable shape having a first planar side surface 63 and an opposite second planar side surface 64 extending parallel to the first side surface 63. In one embodiment, a circumferential, circular surface 66 extends between side surfaces 63 and 64, which are spaced apart a distance substantially equal to the distant between first side surface 58 and second side surface 61 of the slide 57. It is appreciated that, depending on the shape of targeting element, surface 66 can be any other suitable shape including oval or semicircular. Slide 57 includes a recess 67 that is sized and shaped to rotatably receive disk 62 in a manner that the first and second side surfaces 63, 64 of the disk seat substantially flush with the respective first and second side surfaces 58, 61 of the slide 57. In this regard, recess 67 extends through side surfaces 58 and 61 and is formed in part by opposed first and second arcuate surfaces 68, 69 in slide 57, each having a radius substantially equal to the radius of disk 62. Slide 57 has a front face 76 and a rear face 77, and disk 62 is diametrically sized relative to slide 57 such that circumferential surface 66 of the disk extends outwardly from the slide 57 and front face 76 and rear face 77 of the slide 57.

Disk 62 has a bore or passageway 81 extending therethrough for slidably receiving guide sleeve 23. In one embodiment, passageway 81 extends though the disk 62 to opposite first and second openings provided on circumferential surface 66 of the disk. In one embodiment, the passageway 81 extends along an axis 82 centered on a diameter of the disk 62.

Figure 5:
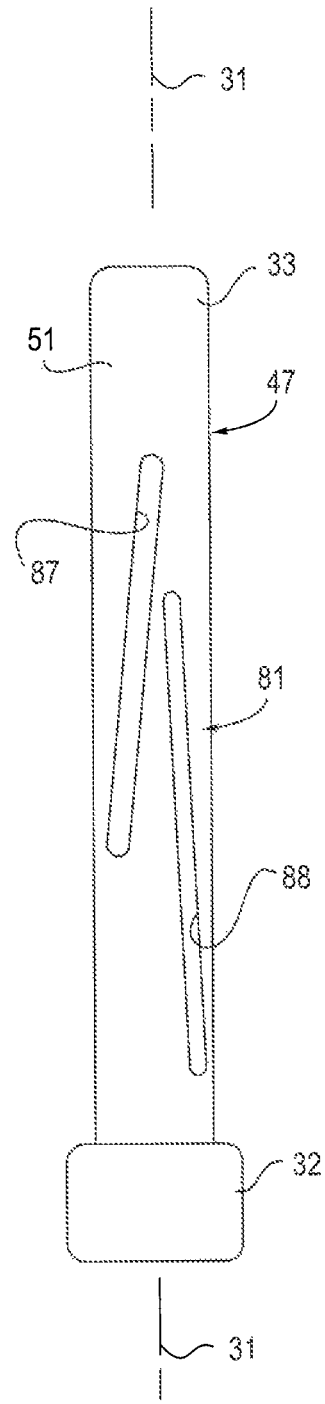
FIG. 5 is a plan view of a guide member of the portion of the implant insertion device illustrated in FIG. 2 and partially visible in FIG. 3.
Figure 6:
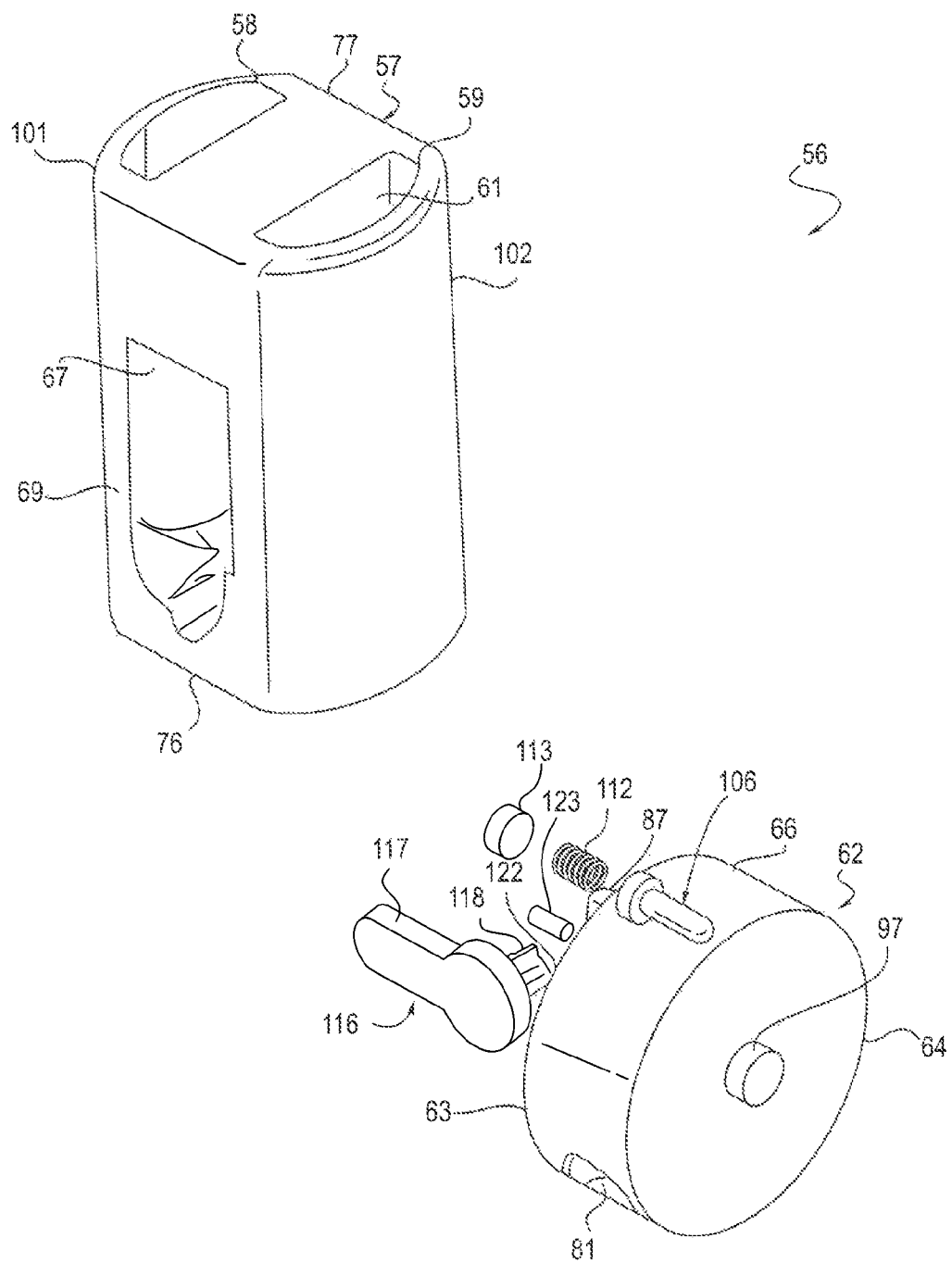
FIG. 6 is an exploded perspective view of a portion of the continuously adjustable targeting assembly of the implant insertion device of FIG. 1.

Targeting portion 28 includes an apparatus for pivoting disk 62 relative to the targeting portion so as to permit the angle of passageway axis 82 relative to longitudinal axis 31 of the targeting portion to be continuously adjusted as carriage 56 is moved upwardly and downwardly along first and second rails 47, 48. In this manner, passageway axis 82 can be pointed towards the intramedullary rod and more specifically towards the aperture 25 in the rod through the continuous range of angular adjustment of the fastener 24 relative to the rod 22. Apparatus 86 includes first and second rails 47, 48 and in one embodiment inner elongate surface 51 of the first rail 47 includes a first groove 87 formed therein and a second groove 88 formed therein (see FIGS. 3 and 5). The first and second grooves or cam grooves 87, 88 are inclined relative to each other and to longitudinal axis 31. In one embodiment, first cam groove or track 87 extends towards the center of the elongate surface 51 as it extends longitudinally upwardly along the rail 47 and second cam groove or track 88, which is lower on the elongate surface 51 relative to the first cam groove 87, similarly extends towards the center of the elongate surface 51 as it extends longitudinally upwardly on the first rail 47. First side surface 63 of the disk 62, which faces inner elongate surface 51 of the first rail 47, has first and second spaced-apart protuberances 91, 92 extending outwardly therefrom. In one embodiment, first protuberance or cam pin 91 extends from surface 63 adjacent circumferential surface 66 and second protuberance or can pin 92 extends from surface 63 adjacent circumferential surface 66 at the opposite end of a diameter of the disk 62 relative to first cam pin 91. As such, first and second cam pins 91, 93 are diametrically opposed on disk surface 63. The transverse dimensions or diameters of the cylindrical can pins 91 and 92 approximates the widths of respective cam grooves 87 and 88, and first cam pin 91 slidable seats within first cam groove 87 and second cam pin 92 slidable seats within second cam groove 88 when slide 57 is slidably carried between the first and second rails 47, 48.

Apparatus 86 further includes a longitudinally-extending groove or guide slot 96 extending along inner elongate surface 52 of the second rail 48. An additional protuberance or guide pin 97 extends from the center of second side surface 64 of the disk 62 and seats within guide slot or pivot slot 96 for permitting rotation of disk 62 between first and second rails 47, 48. Cylindrical guide pin 97 has a diameter approximating the width of guide slot 96, and the guide slot has a length to permit rotation of the disk 62 throughout the longitudinal travel of carriage 56 along rails 47 and 48.

First and second rails 47, 48 and disk 62 have cooperatively engaging features for pivoting the targeting element or disk 62 relative to the first and second rails as the disk slides longitudinally along the first and second rails so as to permit the angle at which the fastener or screw 24 is inserted into the aperture 25 of the rod 22 to be continuously adjusted through an angular range, which can be referred to as a dynamic angular range. In one embodiment, such cooperatively engaging features can include the elongate surface 51 of the first rail 47 and the first groove 87 and the second groove 88 formed in elongate surface 51, and the first side surface 63 of the disk 62 and the first and second protuberances 91, 92 extending outwardly from the side surface of the targeting element or disk 62 for slidably seating in the respective grooves 87, 88. In one embodiment, such cooperatively engaging features can additionally include the elongate surface 52 of the second rail 48 and the groove or guide slot 96 extending along the elongate surface 52, and the second side surface 64 of the disk 62 and the protuberance or guide pin 97 that extends from the second side surface 64 of the disk 62 for slidably seating in the groove or slot 96.

Carriage 56 includes a first cover portion or cover 101 that extends over first rail 47 and secures on its opposite sides to the respective sides of first surface 58 of slide 57. Carriage 56 further includes a second cover portion or cover 102 that extends over second rail 48 and joins to the slide 57 over cutout 59. First and second covers 101, 102, which can each be made from any suitable material such as stainless steel, serve to respectively capture first and second rails 47, 48 within carriage 56 throughout the longitudinal travel of the carriage along rails 47 and 48.

When carriage 56, and disk 62 rotatably carried by slide 57, are slidably mounted on targeting portion 28, first surface 58 of the slide 57 and first side surface 63 of the disk 62 face and slidably engage inner elongate surface 51 of first rail 47, and second surface 61 of the slide 57 and second side surface 64 of the disk 62 face and slidably engage inner elongate surface 52 of the second rail 48. Guide pin 97 of the disk 62 is forcibly restrained on the center line of the inner elongate surface 52 of the second rail 48 throughout the longitudinal travel of the carriage 56 and permits disk 62 to rotate or pivot about an axis (not shown) extending orthogonal to and centered on inner elongate surfaces 51, 52 throughout the longitudinal travel of the carriage 56 on targeting portion 28.

Figure 2:
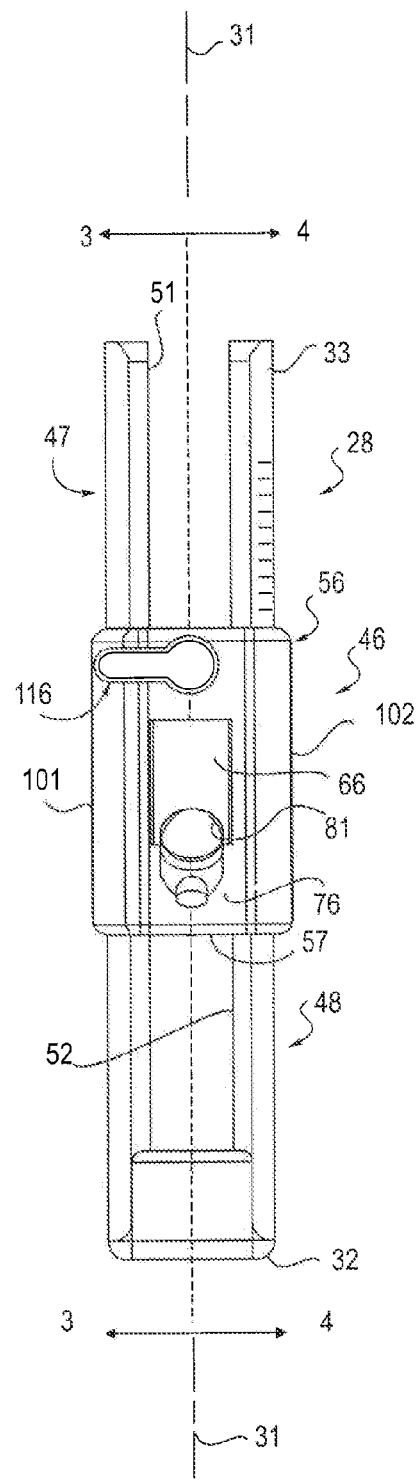
FIG. 2 is an end view of a portion of the implant insertion device of FIG. 1 taken along the line 2-2 of FIG. 1 but with the continuously adjustable targeting assembly in a second position.
Figure 3:
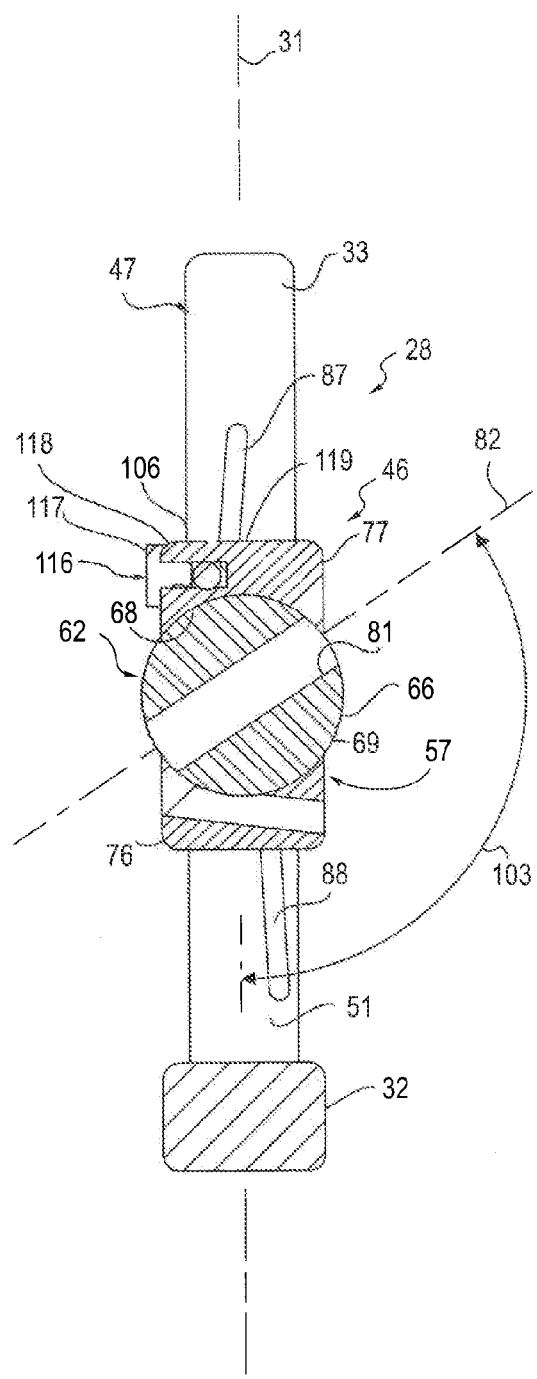
FIG. 3 is a cross-sectional view of the portion of the implant insertion device illustrated in FIG. 2 taken along the line 3-3 of FIG. 2.
Figure 4:
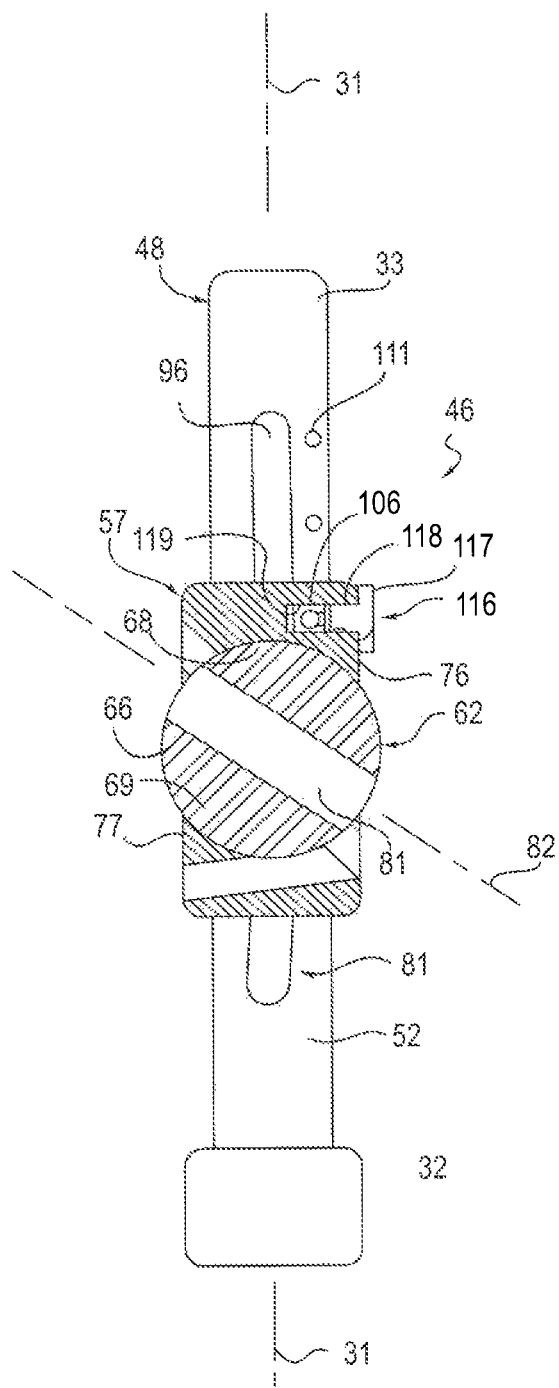
FIG. 4 is a cross-sectional view of the portion of the implant insertion device illustrated in FIG. 2 taken along the line 4-4 of FIG. 2.
Figure 17:
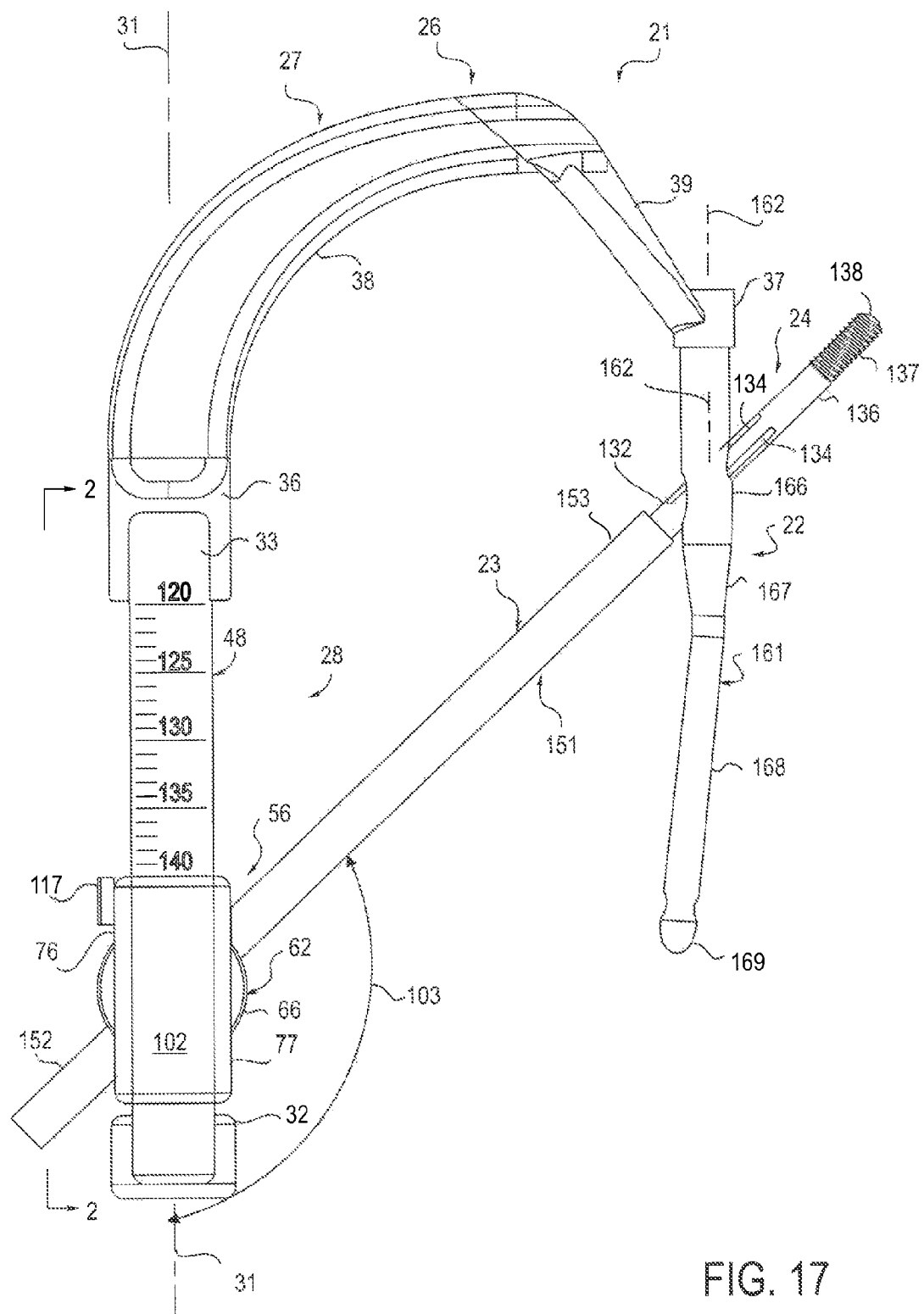
FIG. 17 is a side plan view of the implant insertion device of FIG. 1 with the continuously adjustable targeting assembly in a third position.

The capture of first and second cam pins 91, 92 within respective first and second inclined cam grooves 87, 88 urge the disk 62 to pivot or rotate relative to the rails 47 and 48 and targeting portion 28 as the carriage 56 travels longitudinally along the targeting portion. In one embodiment, the cooperative engagement of cam pins 91 and 92 and respective cam groves 87 and 88 causes disk 62, and passageway 81 extending therethrough, to rotate in a continuous and in one embodiment linear manner as the carriage 56 travels longitudinally from a first position on targeting portion 28 to a second position on the targeting portion. The angular range, which can also be referred to as the dynamic angular range, through which passageway 81 and passageway 81 pivot or rotate relative to the targeting portion can vary. In one embodiment such angular range is at least 5 degrees; in one embodiment such angular range is approximately 10 degrees; in one embodiment such angular range is approximately 20 degrees; in one embodiment such angular range is approximately 30 degrees; in one embodiment such angular range is approximately 40 degrees; in one embodiment such angular range is approximately 50 degrees; in one embodiment such angular range is approximately 60 degrees; in one embodiment such angular range is approximately 70 degrees; and in one embodiment such angular range is approximately 80 degrees. In one embodiment illustrated in the figures, disk 62 and passageway 81 extending therethrough pivot or rotate relative to first and second tails 47, 48 from an angle 103 of approximately 120 degrees when carriage 56 is in a first or upper position on targeting portion 28, as shown in FIG. 1, to an angle 103 of approximately 130 degrees when the carriage is in a second or intermediate position on the targeting portion 28, as shown in FIGS. 2-4, and then to an angle 103 of approximately 140 degrees when the carriage 56 is in a third or lower position on targeting portion 28, as shown in FIG. 17. In this embodiment, the longitudinal travel and carriage 56 and the angular rotation of disk 62 are one-to-one, that is linear.

It is appreciated that cam grooves 87 and 88 can be configured so that the pivoting of disk 62 and passageway axis 81 is non-linear as carriage 56 travels along targeting portion 28, or is non-continuous along a portion of such travel, that is the disk 62 pivots or rotates during some of its longitudinal travel but not at other parts of its longitudinal travel. It is further appreciated that any combination of linear, non-linear and non-continuous rotation or pivoting of disk 62 can be provided by appropriately configuring the shape of first and second cam grooves 87, 88 on respective inner elongate surfaces 51, 52, or by any other suitable means.

As shown in FIGS. 1 and 17, suitable indicators which can include numbers, lines, markings or combinations of numbers, lines and markings can be provided on the outside of at least one of rails 47 and 48 for indicating the angle of passageway 81 and passageway axis 82 at some or all of the positions of carriage 56 on the rails 47 and 48 and targeting portion 28. As can be appreciated, the angle of the passageway 81 is the same as the angle of the guide sleeve 23 and the fixation screw 24 mounted on the end of the guide sleeve 23 relative to the targeting portion 28.

Figure 8:
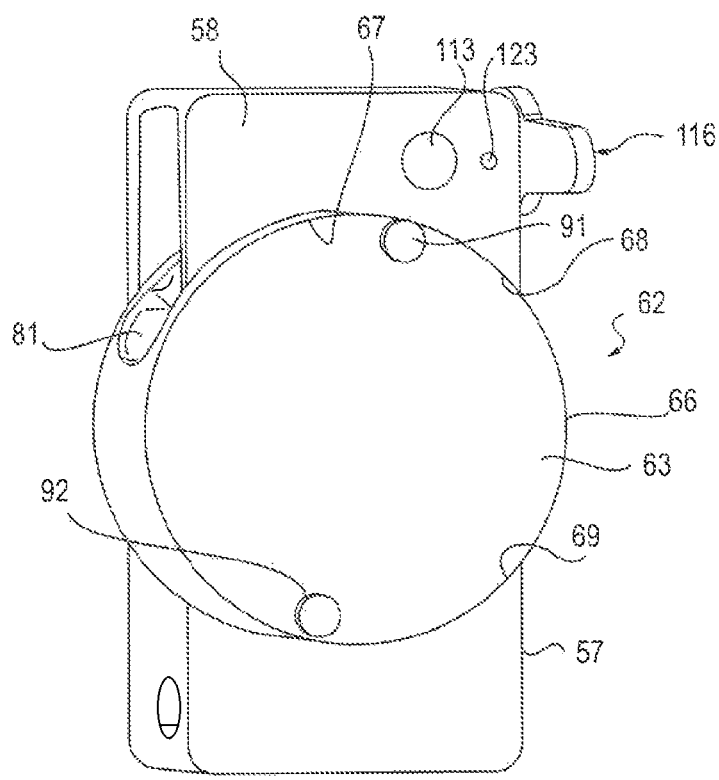
FIG. 8 is a second side perspective view of a portion of the continuously adjustable targeting assembly of the implant insertion device of FIG. 1 with a portion of the housing removed.
Figure 9:
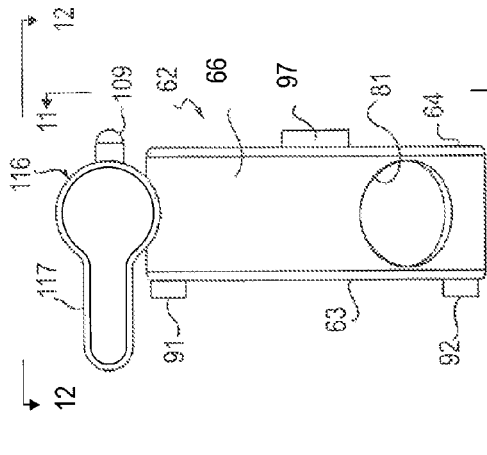
FIG. 9 is a first side view of a portion of the continuously adjustable targeting assembly of the implant insertion device of FIG. 1 with the housing removed.
Figure 11:
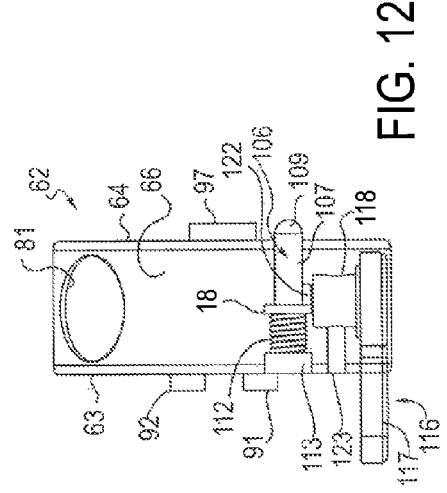
FIG. 11 is a second side view of the portion of the continuously adjustable targeting assembly of FIG. 9 taken along the line 11-11 of FIG. 10.
Figure 10:
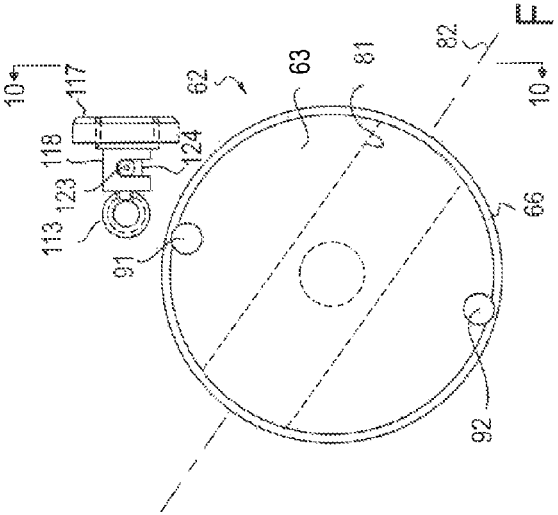
FIG. 10 is a front view of the portion of the continuously adjustable targeting assembly of FIG. 9 taken along the line 10-10 of FIG. 9.

A mechanism or assembly can be included in implant insertion device 22 for locking carriage 56 on certain or any positions along targeting portion 28. In one embodiment, a detent pin 106 having a stem 107 extending from an enlarged head 108 and having a rounded end 109 is provided in slide 57 such that the rounded end 109 retractably extends outwardly from second surface 61 of the slide 57 (see FIG. 7). The rounded end 109 of the detent pin 106 selectively seats with one of a plurality of longitudinally spaced-apart detent holes 111 provided in inner elongate surface 52 of the second rail 48 (see FIG. 4). Any suitable spacing can be provided between detent holes 111, so as to permit locking the disk 62 and passageway 81 at any suitable angular interval. The detent pin 106 is urged to its extended position, in which rounded end 109 extends outwardly from second surface 61 of the slide 57 into one of holes 111, by means of a spring 112 disposed in slide 57 between head 108 of the pin and a plug 113. Pin 106, spring 112 and plug 113 are each disposed within a bore (not shown) extending from first surface 58 to second surface 61 of the slide 57. Plug 113 is secured within such bore and seats flush with first surface 58, as illustrated in FIG. 8.

Figure 12:
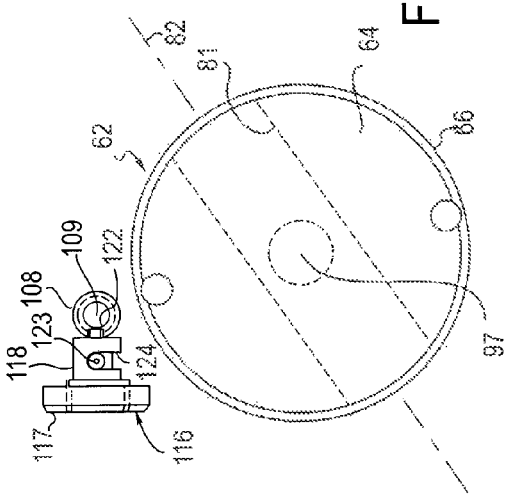
FIG. 12 is a top view of the portion of the continuously adjustable targeting assembly of FIG. 9 taken along the line 12-12 of FIG. 10.

A locking or other suitable element 116 is provided in carriage 56 for urging or moving rounded end 109 of the detent pin 106 against the force of spring 112 from its first or extended position, in which the rounded end extends outwardly from second surface 61 of the slide 57, to its second or retracted position, in which the rounded end is seated flush with or recessed within the second surface 61. In one embodiment, locking element 116 has a lever 117 accessible at front face 76 of the slide 57 and a cylindrical stem 118 which extends into a bore 119 provided in front face 76 of the slide 57. An off-centered pin 122 extends distally from one side of the end of stem 118 and engages the underside of head 108 of the pin 106 (see FIG. 12). As lever 117 is rotated clockwise relative to front face 76 though an angle of approximately 180 degrees, the off-centered pin 122 causes the detent pin 106 to retract within slide 57. A cylindrical pin or rotation limiter 123 extends from first surface 58 of the slide 57 through a bore (not shown) in the slide 57 to engage a semi-annular recess 124 provided in stem 118 of the locking element 116. The engagement of rotation limiter 123 with the end surfaces of the recess 124 limits the rotational travel of the locking element 116 and lever 117 thereof to its desired 180 degrees of angular travel. The rotation limiter 123 further serves to retain stem 118 of the locking element 116 within slide 57, so as to secure the locking element to the slide.

Fastener or screw 24 for use with implant insertion device 21 and intramedullary rod 22 can be of any suitable type and in one embodiment is made from an elongate cylindrical body 131 or spiral blade (not shown) having a length ranging from 40 to 200 millimeters and a diameter ranging from two to 20 millimeters. In one embodiment, the fastener is a fixation screw formed from a body having a threaded portion and a smooth portion. The elongate body 131 can be formed from any suitable material such as stainless steel and include a proximal portion 132 having any outer cylindrical or irregular-shaped surface 133. The proximal portion 132 may be provided with a plurality and as shown four longitudinally-extending slots 134 extending through the surface 133 in circumferentially-spaced apart positions. Distal portion 136 of the body 131 may be provided with external threads 137 that extend to a sharpened distal end or tip 138 of the body. Alternatively, the distal portion 136 of the body 131 may be irregularly shaped or flat (not shown). The body can be provided with a central bore 142 that extends longitudinally through the body 131 from the proximal portion 132 to the distal end or tip 138. The proximal end of the central bore 142 may be provided with internal threads 143 and be formed with a drive socket 144 of any suitable type for facilitating connection of the proximal fixation screw to a drive tool of any suitable type. The proximal end of the body 131 can be formed with a suitable flanged head 146 that has a transverse dimension that is slightly larger than the transverse dimension of the remainder of the body 131 and, as such, limit the longitudinal travel of screw 24 within aperture 25 of the intramedullary rod 22 during operation and use of rod 22 and screw 24 within a suitable bone of a mammalian body.

Guide or alignment sleeve 23 can be of any suitable type and in one embodiment is formed from a cylindrical member or body 151 made from any suitable material such as stainless steel. Body 151 of guide sleeve or overtube 23 has a proximal portion 152 and a distal portion 153. At least proximal portion 152 has a circular cross section and in one embodiment the entire length of the body 151 is circular in cross section. Passageway 81 of disk 62 has a diameter that approximates and is at least slightly larger than the cross sectional dimension of body 151 and as such approximates and is at least slightly larger than the diameter of any circular cross section of the body 151. Body 151 can provided with a central bore 154 extending therethrough so as to be tubular in conformation. The distal end of body 151 can include a suitable drive portion or element (not shown), for example a threaded extension for cooperatively connecting with internal threads 143 provided at the proximal end of screw 24 so as to permit the screw 24 to be connected to the distal end of the guide sleeve 23 and permit the screw 24 to be rotated or driven by the guide sleeve during placement of the screw 24 within a bone.

One embodiment of an implantable medical device suitable for use with implantable insertion device 21 discussed above is apparatus or device or intramedullary rod 22 illustrated in FIGS. 13-16. Although rod 22 can be used in any bone of a mammalian body, in one embodiment rod 22 is for use in a femur and may thus be called a femoral nail 22. Nail 22, described in U.S. nonprovisional application Ser. No. 13/716,079 entitled Implantable Device with Locking Adjustment Mechanism and Method for Using Same filed Dec. 14, 2012, the entire content of which is incorporated herein by this reference, includes an elongate body 161 that extends along a longitudinal or central axis 162 and can have a proximal portion or proximal end or head 166, a central portion or neck 167 and a distal portion or shaft 168 that terminates at a distal tip 169. The nail 22 is illustrated schematically in the figures, where head 166, neck 167 and shaft 168 are not necessary drawn to scale. Body 161 may curve in at least one portion of shaft or stem 168 to align the rod 22 along the length of the marrow canal of the femur or other bone in which the rod is to be inserted. Elongate body 161 can be provided with a longitudinally-extending passageway or bore 176 for permitting the rod to slide along a guide wire (not shown) during insertion of the rod into the femur or other bone of the mammalian body. Furthermore at least one bore 177 can be provided in the distal end portion of stem 168 adjacent tapered tip 169 for receiving at least one distal fastener or screw (not shown).

Figure 16:
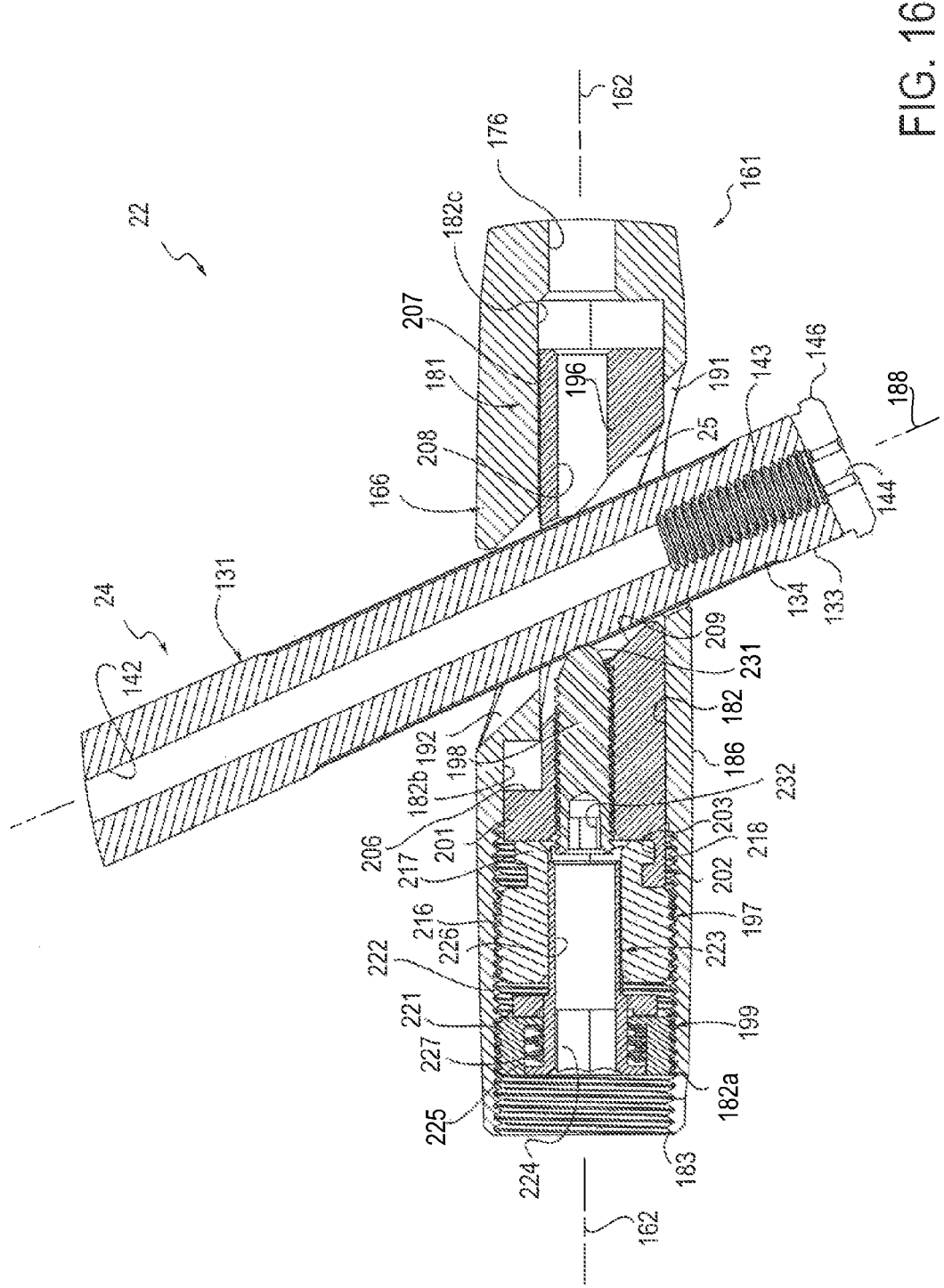
FIG. 16 is an enlarged cross sectional view of the intramedullary rod with a pivotable fastener of FIG. 13 taken along the line 16-16 of FIG. 15.

Head 166 of rod 22 may include an actuation or adjustment mechanism or assembly 181 for selectively pivoting proximal fixation screw 24 from a first angled position relative to the nail head 166 to a second angled position relative to the nail head. In this regard and as illustrated in FIG. 16, the proximal portion central passageway 176 of the nail 22 can be hallowed to form a longitudinally-extending proximal recess 182 that communications with proximal opening 183 in the proximal end of the head 166. Proximal recess 182 can have a proximal or internally-threaded portion 182a adjacent proximal opening 183, a circular central portion 182b and a distal portion 182c that in one embodiment is noncircular in cross section and sometimes referred to herein as the segmented circular portion or segmented portion 182c. Tubular head 166 is formed by an outer wall 186, which is substantially annular in shape and formed by the proximal recess 182.

Head 166 is provided with at least one aperture 25 extending along as transverse axis 188 inclined at an angle to longitudinal axis 162. Head 166 is adapted to receive fastener or screw 24 in aperture 25, which is distinct from proximal recess 182 of elongate passageway 176 but formed in part by the proximal recess 182. In one embodiment, head 166 is provided with a single aperture 25. The aperture 25 can formed by a first or lateral transverse opening 191 provided on one side of wall 186 and a second or medial transverse opening 192 provided on the other side of the wall 186. Transverse axis 188 is centered on aperture 25 and can extend relative to longitudinal axis 162 at an angle and in one embodiment at an angle of approximately 140 degrees measured from the portion of head 166 distal of head aperture 25.

Although the actuation or adjustment mechanism 181 for pivoting the proximal fixation screw 24 can be of any suitable type, in one embodiment mechanism 181 includes an insert, element or sleeve 196, a threaded element or control element 197, an alignment or set screw 198 and a locking mechanism 199. Unless otherwise indicated, each of these components can be made any suitable material such as stainless steel.

Sleeve 196, which in one embodiment is one example of the broad categories of elongate elements or movable elements, can be formed from an elongate tubular element or member having at its proximal portion or end portion a circular annulus or ring 201. A lip 202 is spaced proximally from annulus 201 by a recess 203. Annulus 201 forms the periphery of the sleeve 196 and is substantially circular in shape. Sleeve 196 is provided with an elongate cutout 206 extending distally of annulus 201 for forming distal portion 207 of the sleeve 196. In one embodiment, the distal portion 207 is noncircular in cross section and in one embodiment has a cross section that corresponds generally with the cross section of segmented portion 182c of the head proximal recess 182. Distal portion 207 of the sleeve 196 is sized and shaped to slidably move longitudinally within segmented circular portion 182e of the proximal recess 182 of the head 166. Annulus 201 of the sleeve of 196 is externally sized and shaped to slidably move longitudinally move within central portion 182b of the head proximal recess 182. A passageway or bore 208 extends the length of the sleeve 196. In one embodiment, bore 208 is internally threaded at its proximal portion. Sleeve 196 is provided with at least one aperture 209 in its distal portion 207 that is adapted to receive fastener or fixation screw 24. Aperture 209 is distinct from bore 208, and the bore 208 extends through the aperture 209. In one embodiment, sleeve 196 is provided with a single aperture 209.

Rotatable control element 197, which in one embodiment is one example of the broad categories of elements which include control elements, movable elements and threaded elements, is carried by head 166 and accessible at proximal opening 183 for causing the adjustment mechanism 181 to pivot fixation screw 24 relative to the head 166. The control element can be of any suitable type and in one embodiment includes a spindle, screw or worm gear 197 having first or proximal portion 216 that can be annular and externally threaded for threadable engagement with threaded portion 182a of proximal recess 182 of the head 166. The distal portion or end portion of the worm gear 197 can include an annular flange 217 spaced from externally-threaded proximal portion 216 by an annular recess 215. The flange 217 is diametrically sized and shaped to snugly seat within recess 203 of the sleeve 196. Similarly, annular recess 215 of worm gear 197 is diametrically sized and shaped to snugly receive lip 202 of the sleeve 196. When worm gear 197 is coupled or connected to sleeve 196 in this manner, the central axis of the worm gear is coincident with the central axis of the sleeve 196 and the worm gear is longitudinally fixed or locked relative to the sleeve 196, but the worm gear 197 is rotatable about such central axes and longitudinal axis 162 relative to the sleeve 196.

The worm gear 197 controls the longitudinal position and movement of sleeve 196 when such elements are disposed within head 166, and in this regard the worm gear can be provided with a central passageway or drive socket 218 that extends longitudinally through the worm gear and has a noncircular cross section of any suitable type or shape. When sleeve 196 and worm gear 197 are so disposed within nail head 166, a suitable drive element seated within drive socket 218 of the worm gear 197 can serve to screw or rotate the worm gear 197 proximally or distally within the internally-threaded portion 182a of head proximal recess 182. Such advancement or withdrawal of the worm gear 197 within head 166 simultaneously causes sleeve 196 to advance or withdraw, in a one-to-one manner with the longitudinal movement of the worm gear 197, in central portion 182h and segmented portion 182c of the head proximal recess 182.

Locking mechanism, assembly or device 199 is coupled to worm gear 197 and configured to preclude rotation of the worm gear relative to head 166 when the locking mechanism is in a first position, shown in FIG. 16, and permit rotation of the worm gear 197 relative to the head 166 when the locking mechanism is in a second position (not shown). Although it is appreciated that locking mechanism 199 can have any suitable configuration and construction for rotatably locking and unlocking worm gear 197 within head 166, in one embodiment the locking mechanism includes a first locking element 221 and a second locking element 222. The second locking element 222 is moveable longitudinally between a first position in which a plurality of circumferentially spaced-apart protuberances or dogs 222a on its proximal surface cooperatively engage a plurality of circumferentially spaced-apart protuberances or dogs 221a on the distal surface of the second locking element 222 so that the second locking element is rotatably locked with the first locking element and a second position in which the plurality of circumferentially spaced-apart dogs of the second locking element 222 are disengaged from the plurality of circumferentially spaced-apart dogs the first locking element 221 so that the second locking element is rotatable relative to the first locking element. In one embodiment, the first locking element can be annular in shape and can be an annular element or nut that can be externally treaded and diametrically sized so as to threadably engage threaded portion 182a of proximal recess 182 in head 166. In one embodiment, the second locking element 222 can be annular in shape and can be an annular element or washer.

Locking mechanism 199 can further include a driver element or driver 223 having a drive socket 224 that extends longitudinally inwardly from its proximal end. Socket 224 has a cross section which is non-circular in shape so that when the socket 224 is engaged by a suitable tool it can serve to cause rotation of the driver 223. A longitudinally-extending bore 226 extends distally from drive socket 224 through the remainder of the driver 223. The driver 223 extends through nut 221 and washer 222 and the washer 222 is secured to the proximal portion of the driver 223 by any suitable means such as welding. Nut 221 is not secured to driver 223 and thus longitudinally moveable relative to the driver. Means is included with locking mechanism 199 for urging washer 222 towards its first or locking position relative to nut 221, and can include a suitable spring, for example an annular wave spring 227 disposed around driver 223 and engaging a first flange 225 provided at the proximal end of the driver 223 and a second flange provided on the distal end of the nut 221. Spring 227 urges locking mechanism 199 towards its first or rest position, illustrated in FIG. 16, in which washer 222 is rotatably locked relative to the nut 221.

When driver 223 is urged longitudinally in a distal direction, for example by insertion of a suitable drive tool in drive socket 224 of the driver 223 and exertion of a longitudinal force in the distal direction on the tool and thus the driver 223, washer 222 that is rigidly secured to the proximal portion of the driver 223 is moved longitudinally against the force of spring 227 away from nut 221 so that the dogs of the washer 222 separate and disengage from the dogs of the nut 221 so that the combined driver 223 and washer 222 unit can be rotated relative to nut 221.

Set screw 198 can be of any suitable type and in one embodiment is cylindrical in conformation and externally threaded. The set screw 198 can include a rounded distal end 231 and a suitable drive socket 232 provided at its proximal end. Such set screw is diametrically sized so as to be capable of being passed longitudinally through drive socket 224 and bore 226 of drive 223 and into bore 208 of the sleeve 196 to threadably engage the threaded proximal portion of the sleeve bore 208.

In operation and use, implant insertion device 21 can be utilized for placing nail 22 within a bone in any suitable manner and for example as discussed above. In one method of the invention, end portion or connector 37 of the device is coupled to head 166 of the nail in any suitable manner for inserting the nail 22 into a bone of a mammalian body. In one method, a guide wire is first introduced into the bone and the nail is then threaded over the proximal end of the guide wire for proper placement and positioning in the bone. In this regard, the proximal end of the guide wire can be inserted through passageway 176 of the elongate body 161, though adjustment mechanism 181 by means of bore 208 of sleeve 196 and drive socket 218 of worm gear 197, and through locking mechanism 199 by means of bore 226 and drive socket 224 of driver 223. After the nail 22 has been properly positioned within the bone, the guide wire is removed from the nail 22 through proximal opening 183.

A suitable fastener such fixation screw 24 can be introduced through head 166 by means of lateral transverse opening 191, aperture 209 of sleeve 196 and medial transverse opening 192 and properly positioned within the bone. In this regard, fixation screw 24 is inserted through the distal end of guide sleeve 23 in a suitable manner, for example as discussed above, and in one embodiment the screw 24 extends from the distal end of the guide sleeve 23 so as to be mounted on the distal end of the guide sleeve 23. In one embodiment, the screw extends coaxially with the guide sleeve 23. The guide sleeve 23, before inserting of the screw 24 through the sleeve 23, is introduced through passageway 81 of disk 62. Further advancement of the guide sleeve 23 through the disk passageway 81 targets the distal tip 169 of the screw 24 into the aperture 25 in the head 166 of the nail 22. Regardless of the position of carriage 56 on rails 47 and 48, the guide sleeve 23 and fixation screw 24 are aligned and directed at aperture 25 of the nail 22. In this regard, targeting assembly 46 is configured to rotate disk 62 and guide sleeve 23 carried there the disk relative to the targeting portion 28 of device 21 and to simultaneously move the guide sleeve 23 longitudinally relative to the targeting portion 28 as the guide sleeve is pivoted relative to aperture 25 of the intramedullary nail 22.

Once the fixation screw 24, with the assistance of guide sleeve 23, has been introduced through aperture 25 of the nail 22, and either partially or fully placed within the bone of the mammalian body, the fixation screw 24 can be pivoted relative to head 166 and central axis 162 of the nail through a range of angles by means of adjustment mechanism 181 in the nail 22. In this regard, control element or worm gear 197 can be accessed through connector 37 of implant insertion device 21 and proximal opening 183 at the proximal end of head 166, for example by insertion of a suitable drive tool (not shown) through connector 37 and through opening 183 and then into proximal recess 182 and drive socket 224 of nut 221. In order to rotatably unlock locking mechanism 199 and worm gear 197 that rotates one-to-one with driver 223 of the locking mechanism, so as to permit longitudinal movement of sleeve 197 within head 166, the drive tool is urged distally in drive socket 224 relative to head 166 so as to cause the driver 223 to move longitudinally along axis 162 and thus cause the locking dogs on the washer 222 to longitudinally separate and disengage from the locking dogs of the nut 221 in the manner discussed above. Once the combined driver 223 and washer 222 unit have been moved to a second position of locking mechanism 199, the drive tool can be used to rotate driver 223 freely of nut 221 and head 166 so as to rotate worm gear 197 and thus cause the worm gear and sleeve 196 coupled to the worm gear to move longitudinally within recess 182. In this regard, since the portion of the fixation screw 24 extending through aperture 209 is constrained by sleeve 196, longitudinal movement of the sleeve relative to head 166 causes the fixation screw to pivot about medial transverse opening 192 of the head 166. In this manner, the actuation assembly 181 serves to change the transverse axis 188 of nail aperture 25.

Figure 18:
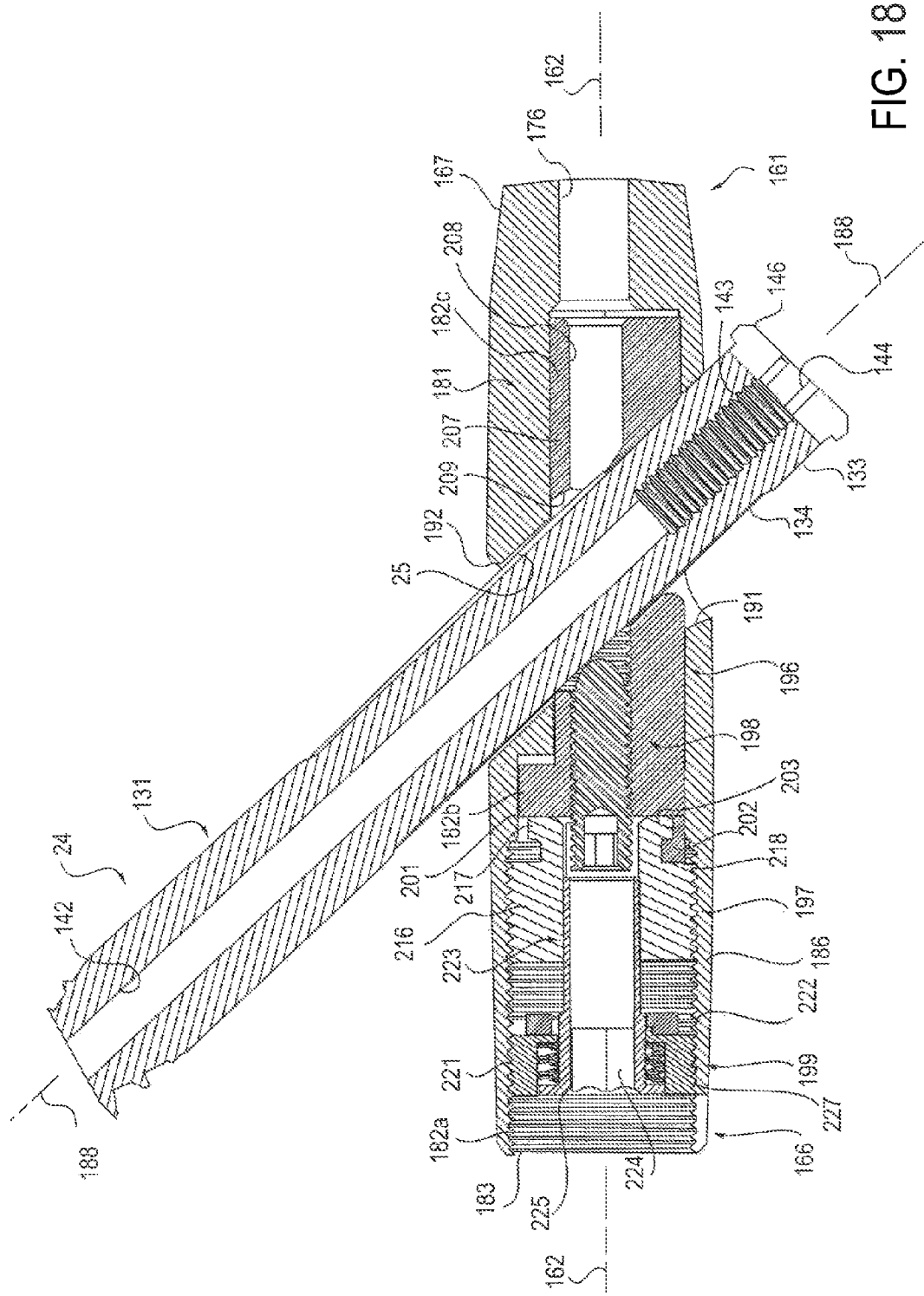
FIG. 18 is an enlarged cross sectional view, similar to FIG. 16, of the intramedullary rod of FIG. 13 with the pivotable fastener in a second position as shown in FIG. 17.

In one embodiment, fixation screw 24 can be pivoted from a first or first extreme position, for example at an angle of approximately 120 degrees relative to head 166 of the nail 22 as shown in FIGS. 13-16, to a second or second extreme position, for example at an angle of 140 degrees relative to head as shown in FIG. 18. In one embodiment, targeting assembly 46 causes disk 62 and passageway 81 extending through the disk to pivot or rotate through the same angular range that fixation screw 24 can be pivoted relative to the intramedullary nail 22. The position of carriage 56 can be moved on rails 47 and 48 during or commensurate with the adjustment of the angular position of the screw 24 within head 24 so that the guide sleeve 23 remains supported by the device 21 and similarly angled as the fixation screw 24 during the procedure.

Once the fixation screw 24 has been desirable angled relative to nail 22, set screw 198 can be inserted through the driver 223 into the internally threaded proximal portion 208a of sleeve bore 208 and advanced distally until the rounded end 231 of the set screw engages the fixation screw 24 to lock the fixation screw in its desired angled position and inhibit further pivoting or rotation of the screw 24 within apertures 25 and 209. In one embodiment, rounded end 231 of the set screw 198 seats within one of the longitudinal slots 204 of the fixation screw 24 for enhancing the rotatable locking of the screw 24 within nail head 166.

The pivoting of the disk 62 relative to the targeting portion 28 when the guide sleeve 23 is disposed in the passageway 81 of the disk permits the angle at which the fixation screw is inserted into the nail aperture 25 to be continuously adjusted through an angular range. As a result, the guide sleeve 23 need not be withdrawn from the targeting portion 28 as with some currently provided implant insertion devices, or a second implant insertion device having a different static angle for the guide sleeve 23 coupled to the nail 22 as with other implant insertion systems, to change the angle at which the guide sleeve 23 and fixation screw 24 are directed at the nail head 166 and the aperture 25 in the head 166.

Figure 19:
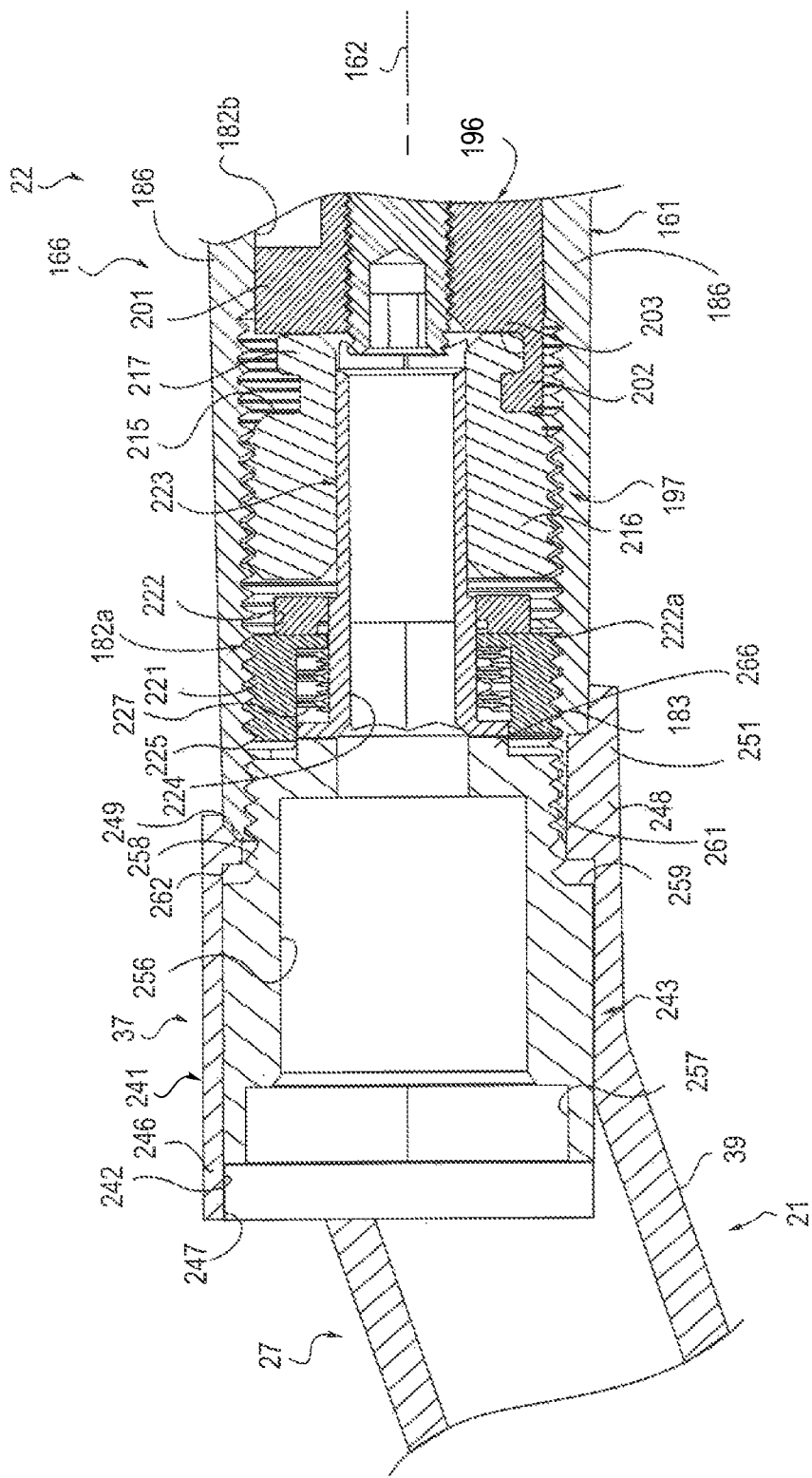
FIG. 19 is an enlarged cross-sectional view of a portion of the implant insertion device of FIG. 1 coupled to the intramedullary rod of FIG. 13 with the locking mechanism of the intramedullary rod in a first position.
Figure 20:
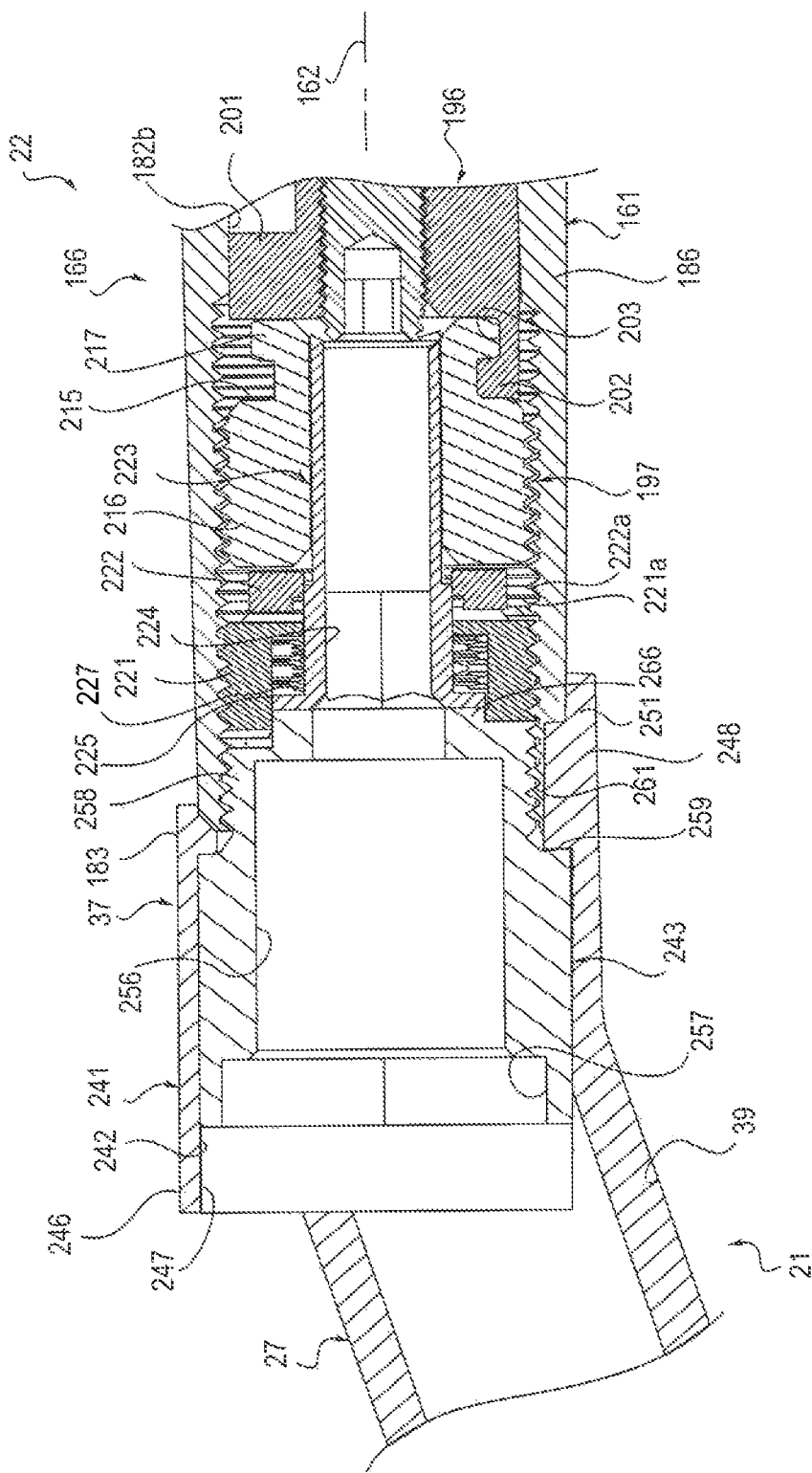
FIG. 20 is a cross-sectional view, similar to FIG. 19, with the locking mechanism of the intramedullary rod in a second position.

One embodiment of the connector 37 of targeting device or jig 21 of the present invention suitable for coupling to a suitable implantable device such as nail 22 is illustrated in FIGS. 19 and 20. Targeting device or jig 21 illustrated therein includes distal portion or arm 27 having goose neck 39 at the distal extremity of the arm 27 and connector 17 at the distal end of the arm 27. In one embodiment, arm 27 terminates at connector 17, which can include a cylindrical or tubular housing 241 provided with a bore or socket 242 for receiving a connector element or fastening element 243. Housing 241 can have a proximal or upper end 246 provided with a proximal or upper opening 247 to socket 242 for permitting the fastening element 243 to be inserted into the socket and a distal or lower end 248 provided with a distal or lower opening 249 through which a portion of the fastening element 243 can extend for securing to the nail head 166.

Lower end 248 of the housing 242 is sized and shaped to cooperatively engage with the proximal end and proximal opening 183 of nail had 166. In one embodiment, the lower opening 249 has a diameter approximating the diameter of the proximal opening 183 of nail head 166. Housing 241 can be further provided with a registering element or key 251 which is cooperatively sized and shaped to snugly seat within a recess or notch 252 provided on the proximal end of the nail head 166 so as to rotatably lock and register the housing 241 and thus targeting device 21 with the nail head 166 and thus nail 22.

Fastening element 243 can be of any suitable type and in one embodiment is a cylindrical nut 243 having a diameter closely approximating but slightly smaller than the diameter of bore or socket 242 in housing 241. Nut 243 can be provided with a through hole 256 extending through the nut 243. A suitable drive socket 257 can be provided at the proximal end of the hole 256 for receiving any suitable drive element (not shown) for rotating the nut 243 within housing 241. The exterior of the distal end 258 of nut 243 necks down to a smaller diameter at annular surface 259 and is provided with external threads 261. The externally-threaded distal end 258 cooperatively engages and threads with internally-threaded portion 182 at the proximal end of nail head 166. Housing 241 is provided with an annular seat or surface 262 in socket 242 for receiving and engaging the annular surface 259 of the nut 243.

When securing targeting assembly or device 21 to nail 22, nut 243 is placed in socket 242 of housing 241 and the housing urged again the proximal end of nail head 166 so that housing key 251 registers with notch 252 in the nail head 166. A suitable drive tool is inserted into drive socket 257 of the nut 243 to screw the external threads 261 of the nut 243 into the proximal opening 183 of the nail head 166. The housing 241 is urged against and secured to the proximal end of the nail head 166 by the engagement of annular surface 259 of the nut 243 with annular seat 262 of the housing 241.

The securing of the connector 17 of the targeting device 21 to the head 166 of the nail 22 automatically causes locking, mechanism 199 of the nail to unlock so as to permit rotation of worm gear 197 and thus movement of sleeve 196 so as to thus permit pivoting of screw 24 relative to the nail 22. In one embodiment, the distal end 258 of nut 243 has a suitable actuation element of any suitable type such as an extension or cylindrical extension 266 which protrudes or extends distally from such end 258 and in one embodiment is centered on the central longitudinal axis of the nut 243, which axis in FIGS. 19 and 20 is collinear with or the same as longitudinal axis 162. The extension 266 can have an external diameter less than the external diameter of the externally-threaded distal end 258. The external diameter of the extension 266 can be less than the internal diameter of nut 221 of the locking mechanism 199 so as to engage flange 225 of driver 223 of the locking mechanism and simultaneously move the driver 223 distally from its first or locked position, illustrated in FIG. 19, to its second or unlocked position, illustrated in FIG. 20, as the nut 243 of the targeting device 21 is screwed into the proximal end of the nail head 166. The actuation element can be a cylinder, piston or plunger, and can be free of external threads. The actuation element can also have other shapes, such as noncircular in cross section relative to the central longitudinal axis of the nut 243.

In the foregoing manner, the mere coupling or connecting of the targeting device 21 to the nail unlocks the locking mechanism 199 of the nail and permits the angle of the transverse aperture 25 of the nail, and thus fastener or screw 24, to be adjusted relative to the central axis 162 of the nail. As discussed above, pivoting of the fastener 24 is caused by inserting a suitable drive element through nut 243 and housing 241 of the connector 37 into drive socket 224 of driver 223. Prior to such connecting of the targeting assembly 21 to the nail 22 or other implantable device, the locking mechanism 199 is in its locked position so as to preclude angular adjustment of transverse aperture 25 or any fastener 24 therein.

It is appreciated that other intramedullary nails, and other implants, can be utilized with the implant insertion device of the present invention. It is also appreciated that other configurations or designs of implant insertion devices can be provided to pivot a guide sleeve through a continuous angular range relative to the implant insertion device and be within the scope of the present invention. It is further appreciated that other configurations or designs of implant insertion devices can be provided that rotate the guide sleeve relative to the implant insertion device and simultaneously move the guide sleeve longitudinally relative to the implant insertion device as the guide sleeve is pivoted relative to an implant, or more specifically relative to an aperture in an implant, and be within the scope of the present invention.

We claim:

1. An implant insertion device for use with an intramedullary rod having a proximal end and an aperture for receiving a fastener, and also with a separate guide sleeve for inserting the fastener into the aperture of the intramedullary rod, the implant insertion device comprising a body having a first portion adapted for coupling to the proximal end of the intramedullary rod and a second portion extending in a spaced position from the intramedullary rod in the vicinity of the aperture when the proximal end of the intramedullary rod is coupled to the first portion, the second portion including a targeting assembly having a passageway for receiving the guide sleeve, the targeting assembly serving to point the guide sleeve at the aperture while directing cooperative angular and longitudinal movement of the guide sleeve during continuous adjustment of the guide sleeve through an angular range as the guide sleeve is moved longitudinally on the second portion.

2. The implant insertion device of claim 1 wherein the angular range is selected from the group consisting of at least 5 degrees, approximately 10 degrees, approximately 20 degrees, approximately 30 degrees and approximately 40 degrees.

3. The implant insertion device of claim 1 wherein the targeting assembly includes an elongate element and a targeting element movable along the elongate element and provided with the passageway for receiving the guide sleeve, the elongate element and the targeting element having cooperatively engaging features for causing the guide sleeve to continuously point at the aperture as the targeting element is moved longitudinally on the elongate element.

4. The implant insertion device of claim 1 in combination with the intramedullary rod, the intramedullary rod extending along a longitudinal axis and having a stem and a head, the head being at the proximal end and being provided with the aperture that extends along an axis at an angle to the longitudinal axis and is adapted to receive the fastener, an adjustment mechanism carried by the head for pivoting the fastener from a first angled position relative to the head to a second angled position relative to the head.

5. An implant insertion device for use with an intramedullary rod having a proximal end and an aperture for receiving a fastener, and also with a separate guide sleeve for inserting the fastener into the aperture of the intramedullary rod, the implant insertion device comprising a body having a first portion adapted for coupling to the proximal end of the intramedullary rod and a second portion extending in a spaced position from the intramedullary rod in the vicinity of the aperture when the proximal end of the intramedullary rod is coupled to the first portion, the second portion including a targeting assembly having a passageway for receiving the guide sleeve, the targeting assembly directing cooperative angular and longitudinal movement of the guide sleeve relative to the second portion so as to continuously point the guide sleeve at the aperture as the angle of the guide sleeve relative to the second portion is continuously adjusted through an angular range.

6. The implant insertion device of claim 5 wherein the angular range is selected from the group consisting of at least 5 degrees, approximately 10 degrees, 20 degrees, 30 degrees and 40 degrees.

7. The implant insertion device of claim 5 wherein the targeting assembly includes an elongate element and a targeting element movable along the elongate element and provided with the passageway for receiving the guide sleeve, the elongate element and the targeting element having cooperatively engaging features for causing the guide sleeve to move longitudinally on the elongate element and continuously point at the aperture as the angle of the guide sleeve relative to the elongate element is adjusted through an angular range.

8. The implant insertion device of claim 7 wherein the targeting element includes an elongate surface and the targeting element has a side surface facing the elongate surface and wherein the cooperatively engaging features include first and second grooves provided in the elongate surface and inclined relative to each other and first and second spaced-apart protuberances extending from the side surface and seating respectively in the first and second grooves whereby as the targeting element moves longitudinally along the elongate surface the travel of the first and second protuberances in the first and second grooves causes the targeting element to pivot relative to the aperture of the intramedullary rod.

9. The implant insertion device of claim 8 wherein the targeting element includes an additional elongate surface and the targeting element is disposed between the first-named elongate surface and the additional elongate surface, the additional elongate surface being provided with a longitudinally-extending groove and the targeting element having an additional side surface facing the additional elongate surface and an additional protuberance extending from the additional side surface and seating in the longitudinally-extending groove, the additional protuberance rotating within the longitudinally-extending groove as the targeting element is moved longitudinally along the elongate surface and the additional elongate surface.

10. An implant insertion device for use with an intramedullary rod having a proximal end and an aperture for receiving a fastener, and also with a separate guide sleeve for inserting the fastener into the aperture of the intramedullary rod, comprising spaced-apart first and second longitudinally-extending rails having a first end portion and a second end portion, an arm having a first extremity secured to the second end portion of the first and second rails and a second extremity adapted for coupling to the proximal end of the intramedullary rod, a targeting element having a passageway for receiving the guide sleeve slidably carried between the first and second rails, the first and second rails and the targeting element having cooperatively engaging features for pivoting the targeting element relative to the first and second rails as the targeting element slides longitudinally along the first and second rails so as to permit the angle at which the fastener is inserted into the aperture of the intramedullary rod to be continuously adjusted through a dynamic angular range.

11. The implant insertion device of claim 10 wherein the angular range is selected from the group consisting of at least 5 degrees, 10 degrees, 20 degrees, 30 degrees and 40 degrees.

12. The implant insertion device of claim 10 wherein the cooperatively engaging features include an elongate surface on the first rail provided with first and second grooves inclined relative to each other, the targeting element having a side surface facing the elongate surface and first and second spaced-apart protuberances extending from the side surface and seating respectively in the first and second grooves whereby as the targeting element moves longitudinally along the elongate surface the travel of the first and second protuberances in the first and second grooves causes the targeting element to pivot relative to the aperture of the intramedullary rod.

13. The implant insertion device of claim 12 wherein the cooperatively engaging features include an elongate surface on the second rail and the targeting element is disposed between the elongate surface of the first rail and the elongate surface of the second rail, the elongate surface of the second rail being provided with a longitudinally-extending groove and the targeting element having an additional side surface facing the elongate surface of the second rail and an additional protuberance extending from the additional side surface and seating in the longitudinally-extending groove, the additional protuberance rotating within the longitudinally-extending groove as the targeting element is moved longitudinally along the elongate surfaces of the first and second rails.

14. An implant insertion device for use with an implantable device having a head with an internally-threaded proximal end and an adjustment mechanism carried by the head and including a rotatable control element accessible at the proximal end and a locking mechanism that precludes rotation of the control element when in a first position and permits rotation of the control element when in a second position, comprising a first portion adapted for connecting to the proximal end of the implantable device and a second portion extending in a spaced position from the implantable device for controlling implantation of the implantable device, the first portion having a rotatable element provided with an externally-threaded distal end for cooperatively engaging the internally-threaded proximal end of the head, the externally-threaded distal end having an external diameter and the rotatable element having an extension that extends distally of the externally-threaded distal end and has an external diameter less than the external diameter of the externally-threaded distal end for engaging the locking mechanism and moving the locking mechanism from its first position to its second position simultaneous with the threading of the externally-threaded distal end into the internally-threaded proximal end of the head.

15. The implant insertion device of claim 14 wherein the extension is a cylinder free of external threads.

16. The implant insertion device of claim 14 wherein the implantable device is an intramedullary nail having an aperture for receiving a fastener and wherein the second portion includes a targeting assembly for receiving a guide sleeve that has a distal portion couplable to the fastener for inserting the fastener into the aperture of the intramedullary rod.

17. An implant insertion device for use with an intramedullary rod having a proximal end and an aperture for receiving a fastener, and also with a separate guide sleeve for inserting the fastener into the aperture of the intramedullary rod, comprising a body having an arm adapted for coupling to the proximal end of the intramedullary rod and a targeting portion extending in a spaced position from the intramedullary rod in the vicinity of the aperture when the proximal end of the intramedullary rod is coupled to the arm, a targeting element having a passageway for receiving the guide sleeve carried by the targeting portion and the targeting portion including an apparatus for pivoting the targeting element relative to the targeting portion when the guide sleeve is disposed in the passageway so as to permit the angle at which the fastener is inserted into the aperture of the intramedullary rod to be continuously adjusted through an angular range, the apparatus including an elongate surface provided with first and second grooves inclined relative to each other, the targeting element having a side surface facing the elongate surface and first and second spaced-apart protuberances extending from the side surface and seating respectively in the first and second grooves whereby as the targeting element moves longitudinally along the elongate surface the travel of the first and second protuberances in the first and second grooves causes the targeting element to pivot relative to the aperture of the intramedullary rod.

18. The implant insertion device of claim 17 wherein the apparatus includes an additional elongate surface and the targeting element is disposed between the first-named elongate surface and the additional elongate surface, the additional elongate surface being provided with a longitudinally-extending groove and the targeting element having an additional side surface facing the additional elongate surface and an additional protuberance extending from the additional side surface and seating in the longitudinally-extending, groove, the additional protuberance rotating within the longitudinally-extending groove as the targeting element is moved longitudinally along the elongate surface and the additional elongate surface.

19. An implant insertion device for use with an intramedullary rod having a proximal end and an aperture for receiving a fastener, and also with a separate guide sleeve for inserting the fastener into the aperture of the intramedullary rod, comprising a body having an arm adapted for coupling to the proximal end of the intramedullary rod and a targeting portion extending in a spaced position from the intramedullary rod in the vicinity of the aperture when the proximal end of the intramedullary rod is coupled to the arm, a disk carried by the targeting portion and having a circumferential surface and a passageway extending through the circumferential surface for receiving the guide sleeve and the targeting portion including an apparatus for pivoting the disk relative to the targeting portion when the guide sleeve is disposed in the passageway so as to permit the angle at which the fastener is inserted into the aperture of the intramedullary rod to be continuously adjusted through an angular range.

20. The implant insertion device of claim 19 wherein the apparatus includes an elongate surface provided with first and second grooves inclined relative to each other, the disk having a side surface facing the elongate surface and first and second spaced-apart protuberances extending from the side surface and seating respectively in the first and second grooves whereby as the disk moves longitudinally along the elongate surface the travel of the first and second protuberances in the first and second grooves causes the disk to pivot relative to the aperture of the intramedullary rod.

21. The implant insertion device of claim 20 wherein the apparatus includes an additional elongate surface and the disk is disposed between the first-named elongate surface and the additional elongate surface, the additional elongate surface being provided with a longitudinally extending groove and the disk having an additional side surface facing the additional elongate surface and an additional protuberance extending from the additional side surface and seating in the longitudinally-extending groove, the additional protuberance rotating within the longitudinally-extending groove as the disk is moved longitudinally along the elongate surface and the additional elongate surface.

* * * * *